(12) United States Patent
Block et al.

US008796200B2

(10) Patent No.: US 8,796,200 B2
(45) Date of Patent: Aug. 5, 2014

(54) OPTIMIZED ADHESIN FRAGMENTS AND CORRESPONDING NANOPARTICLES

(75) Inventors: Christoph Block, Münster (DE); Karin Mittmann, Münster (DE); Claudia Arntz, Lengerich (DE)

(73) Assignee: Signalomics GmbH, Vienna (AT)

( * ) Notice: Subject to any disclaimer, the term of this patent is extended or adjusted under 35 U.S.C. 154(b) by 779 days.

(21) Appl. No.: 12/920,236

(22) PCT Filed: Jun. 17, 2008

(86) PCT No.: PCT/EP2008/004867
§ 371 (c)(1),
(2), (4) Date: Nov. 30, 2010

(87) PCT Pub. No.: WO2009/106102
PCT Pub. Date: Sep. 3, 2009

(65) Prior Publication Data
US 2011/0110856 A1    May 12, 2011

(30) Foreign Application Priority Data
Feb. 29, 2008  (EP) .................................... 08003845

(51) Int. Cl.
*A61K 47/00*       (2006.01)
*A61K 38/00*       (2006.01)
*A61K 38/02*       (2006.01)
*A61K 38/17*       (2006.01)
*C07K 14/705*      (2006.01)
*B82Y 5/00*        (2011.01)
*A61K 49/00*       (2006.01)
*B82Y 15/00*       (2011.01)

(52) U.S. Cl.
CPC ............ *C07K 14/70503* (2013.01); *B82Y 5/00* (2013.01); *A61K 49/0056* (2013.01); *G01N 338/57446* (2013.01); *A61K 49/0067* (2013.01); *B82Y 15/00* (2013.01); *Y10S 530/81* (2013.01)
USPC ............ 514/1.1; 514/21.2; 530/300; 530/810

(58) Field of Classification Search
CPC ....... A61K 38/00; A61K 38/02; A61K 38/17; A61K 49/00; A61K 49/0002; A61K 49/0004; A61K 49/001; C07K 14/00; C07K 17/00; G01N 33/483
See application file for complete search history.

(56) References Cited

U.S. PATENT DOCUMENTS

| | | | | |
|---|---|---|---|---|
| 5,965,710 | A * | 10/1999 | Bodmer et al. ............ | 530/387.7 |
| 6,179,912 | B1 | 1/2001 | Barbera-Guillem et al. | |
| 7,147,712 | B2 | 12/2006 | Zehnder et al. | |
| 2004/0247861 | A1 | 12/2004 | Naasani | |
| 2010/0183504 | A1 * | 7/2010 | Chen ............................ | 424/1.29 |

FOREIGN PATENT DOCUMENTS

| | | |
|---|---|---|
| EP | 1 721 974 A1 | 11/2006 |
| EP | 1 777 292 A1 | 4/2007 |
| WO | WO 2004/003558 | 1/2004 |
| WO | WO 2005/001889 | 1/2005 |
| WO | WO 2007/057182 | 5/2007 |
| WO | WO 2008/074461 | 6/2008 |

OTHER PUBLICATIONS

Arbos et al., Journal of Controlled Release (2002) 83, 321-330.*
Sylvie Hudault et al.: Human Diffusely Adhering *Escherichia coli* Expressing Afa/Dr Adhesins That Use Human CD55 (Decay-Accelerating Factor) as a Receptor Does Not Bind the Rodent and Pig Analogues of CD55; Infection and Immunity, Aug. 2004, p. 4859-4863.
Natalia Korotkova et al.: The Dr Family of *Ecoli*Adhesins bind independently to the Decay-Accelerating Factor and the N-domain of Carcinoembryonic Antigen;J Biol Chem Sep. 29, 2006; 281 (39): 29120-29130. doi: 10.1074/jbc.M605681200.
Natalia Korotkova et al: "Selection for functional diversity drives accumulation of point mutations in Dr adhesins of *Escherichia coil*" in Molecular Microbiology (2007) (64(1), 180-194.
Cedric N. Berger et al:• Differential recognition of members of the carcinoembryonic antigen family by Afai/Dr adhesins of diffusely adhering *Escherichia coli* (Afa/Dr DAEC) Molecular Biology, vol. 52, No. 4, May 2004, pp. 963-983.
X. Gao et al: "In vivo cancer targeting and imaging with semiconductor quantum dots", in: Nature Biotechnology, vol. 22, No. 8, Aug. 2004, pp. 969-976.
Kirstine Anderson et al.: "Letter to the Editor: Complete Resonance assignements of a 'donor-strand complemented' AfaE: The afimbrial adhesion from Diffusely adherent *E.coli*", in: Journal of Biomolecular NMR 29, 409-410, Netherlands, 2004.
Kirstine Anderson et al.: "An Atomic Resolution Model for Assembly, Architecture, and Function of the Dr Adhesins", in: Molecular Cell, vol. 15, 647/657, 2004.
Soisungwan Satarug et al.: "Safe levels of Cadmium Intake to prevent Renal Toxicity in human Subjects", in: British Journal of Nutrition, 84, 791-802, 2000.
Natalia Korotkova et al.: A Subfamily of Dr Adhesins of *Escherichia coli* Bind independently to Decay-accelerating Factor and the N-domain of Carcinoembryonic Antigen, in: The Journal of Biological Chemistry, vol. 281, No. 39, 2006.
Cedric N. Berger et al.: "Differential recognition of member of the carcinomembryonic antigen family by Afa/Dr adhesions of diffusely adhering *Escherichia coli* (Afa/Dr DAEC)", in: Molecular Microbiology, 963-983, 2004.
Alain L. Servin: "Pathogenesis of Afa/Dr Diffusely adhering *Eschericia coli*", in: Clinical Microbiology Reviews, 264-292, 2005.
Rafal Piatek et al.: "Molecular Aspects of Biogenesis of *Escherichia coli* Dr Fimbriae: Characterization of DraB-DraE Complexes", in: Infection and Immunity, 135-145, 2005.
Cristina P. Van Loy et al.: "Identification of Amino Acids in the DR Adhesin required for binding to decay/accelerating Factor", in: Molecular Microbiology, 439-452, 2002.

\* cited by examiner

*Primary Examiner* — Karlheinz R Skowronek
*Assistant Examiner* — Catherine Mader
(74) *Attorney, Agent, or Firm* — Taroli, Sundheim, Covell & Tummino, LLP

(57) ABSTRACT

The invention relates to optimized adhesins and nanoparticles to which said adhesins are bound. The invention furthermore relates to providing said nanoparticles by way of in vivo contrast agents, in particular for the diagnosis of bowel cancer.

9 Claims, 16 Drawing Sheets

Fig. 1 ; SEQ ID No 1

```
GFTPSGTTGT TKLTVTEECQ VRVGDLTVAK TRGQLTDAAP IGPVTVQALG    50
CDARQVALKA DTDNFEQGKF FLISDNKRDK LYVNIRPTDN SAWTTDNGVF   100
YKNDVGSWGG IIGIYVDGQQ TNTPPGNYTL TLTGGYWAK              139
```

Fig. 2

CLUSTAL 2.0.8 multiple sequence alignment of in each case one representative of each adhesin group (acc. to Korotkova, 2007)

```
AfaE-5      AFTGSGSTGTGTKLTVTEQCQVLVTGSD--VTKTRGELITDGARVGVLSVTAKGCNT-EHAA   57
DrbE-122    AFTASGNTGTKLTVTEQCQVMVTGSA--STKTRGELIDGARVGALSLNARGCNT-EHAA     57
DraE        GFTPSGTTGTKLIVTEECQVRVGDLT--VAKTRGQLTDAAPIGPVTVQALGCDA-RQVA     57
SM254       QFSYSGNTGTKVTVTEECQIQVGDFS--TTKPRSQLTNGAAIGPINVTARGCDT-RQIA     57
DaaE        TFQASGTTGITLTVTEECRVQVGNVT--ATLARSKLKDDTAIGVIGVTALGCNG-LQAA     57
AfaE-2      -AVDKHATGYTLNVTEECAVHLTDNT--ESLRKTDLTEGKLLAGVGLSATGCAN-SKVA     56
AfaE-1      NFTSSGTNGKVDLTITEECRVTVESKS--ESFLRSGLVANRHITNLGIQSTGCGTGQRVA    58
NfaE-111    GIRLGTATASGTITNNMESCTVNLTIATPDAKMNRAGMQENREITKFKVASNDCFTDTYAV   60
                 :        *  .*:   . .   *                    :::    .*

AfaE-5      LRAQPDNYHQGK-IVLIRDDYQARINVRLQAT------DGRAUNTNGDTVYRADAGNWGG5   111
DrbE-122    LRAQADNYHNGK-IVLLREDQQARINVRLVAS------DGGGQUTNDGATTYRDALGDWGGS   111
DraE        LKADTDMFEQGK-FFLISDNNRDKLYVNIRPT------DNSANTTDNGVFYKNDVGSWGGI   111
SM254       LQAGADNIEGDK-LYMRSDNGGDKLYVVLSAL------DGSNWTTDNGVFYNTVPGNWGGT   111
DaaE        LQADPDNYDATN-LYMTSRN-HDKLNVKLKAT------DGSSWTYGNGVFYKTEGGNWGGH   110
AfaE-2      FSADAGNLKGTN-ILLKGADKTSFPVYWETATAAGDDSHNWTATTEGLHRNSNGPWEGT    115
AfaE-1      LKLGAGSYDDTNGAHMTHENGTDKLLVSNGSA------TGDGTQDGGVYYINRDCNWNGQ   112
NfaE-111    WFKEIDNVANGI--AQGKSEYQTRFYLRWAST------NGTESQKDISVGNKTGKGLSGKL   113
             :  .            :                             *

AfaE-5      LF------VVVDCDNVDKPTGSYTLNLDWGVWVS    139
DrbE-122    LY------VVVDGDNTSNQAGSYTLNNDGGYWAS    139
DraE        IG------ILYVDGQQTNTPPGNYTLTLTGGYWAK   139
SM254       IG------VKVQGDQTRTPTPGNYTLTLTGGYWAK   139
DaaE        VG------ISVDGNQTDKPTGEYTANLTGGYWTN   138
AfaE-2      IR------LRVIGDQTSAKAQAYTLVLNGGTWIE   143
AfaE-1      NV------FIVRNDQQHLPTGKYTLNLEGGFWTK   140
NfaE-111    ANGAPEGKITLAQDTTGVPVDVYTNLMAAVYSQ   147
            :                                   
                        : . :. ::  .        .

without signal sequence
```

Fig. 3 , SEQ ID No 2

```
XXXXXXXXXXXXXXXXEXCXXXXXXXX--XXXXXXXXXXXXXXXXXXXXXXCXX-
XXXXXXXXXXXXXXX-XXXXXXXXXXXXXXXXXX-----
XXXXXXXXXXXXXXXXGXXXXXXX------XXXXXXXXXXXXXXYTXXXXXXXXX
```

Fig. 4

GFTPSGTTGTTKLTVTEECQVRVGDLTVAKTRGQLTDAAPIGPVTVQALGCXARQVALKAXT
DNFEQXKFFLISDNKRDKLYVNXRPXDNSXWTTDNGVFYKNDVGSWGGXIGIYVDGQQTNTP
PGNYTLXLTGGYWAK

Fig. 5 , SEQ ID No 3

GFTPSGTTGTTKLTVTEECQVRVGDLTVAKTRGQLTDAAPIGPVTVQALGCXARQVALKADT
DNFEQGKFFLISDNNRDKLYVNIRPXDNSAWTTDNGVFYKNDVGSWGGXIGIYVDGQQTNTP
PGNYTLTLTGGYWAK

*Fig. 6*
*SEQ ID No 4*

```
XXXXXXXPXXXAEGKXVLLXXXNXXXXXXXYXWXKGXXXXXXXXXIXGYXXXX-
QXXXPGXAXXXREXXYXNXXLLXXNXXXXDXGXYTLXXIXXXXXXXXXTXQXXVXXXXXXPX
XXXXXXXXXXXXXXVXXXXXXXXXXXXXLXXXXXSXXXXXXXXXXXXXXXXXXXXXXXXX
XXXXXXXXXXXAXXXXXXXXXXXYXX
```

Fig. 7
SEQ ID No 5

Fig. 8

KLTIESTPFNVAEGKEVLLLXHNLPQXXXGYSWYKGERVDGNXXIXGYVIGTQQATPGPAYS
GREXIYPNASLLIQNXXQNDTGFYTLXVIKSDLVNEEATGQFXVYPELPKPSISSNNSXPVE
DKDAVAFTCEPEXQXXTYLWWVNXQSLPVSPRLQLSNGNXTLTLXXVXRNDXXSYXCEXQNP
XSAXRSDXVXLNVLYGPDXPTISPXXXXYRXGENLNLSCHAASNPPAQYSWFXNGTFQQSTQ
ELFIPNITVNNSGSYXCQAHNSXTGLNRTTVTXITVYAEPPKPFITSNNSNPVEDEDAVALT
CEPEIQNTTYLWWVNNAHNSATGLNRTTVTMITVQSLPVSPRLQLSNDNRTLTLLSVTRNDV
GPYECGIQNELSVDHSDPVILNVLYGPDDPTISPSYTYYRPGVNLSLSCHAASNPPAQYSWL
IDGNIQQHTQELFISNITEKNSGLYTCQANNSASGHSRTTVKTITVSAELPKPSISSNNSKP
VEDKDAVAFTCEPEAQNTTYLWWVNGQSLPVSPRLQLSNGNRTLTLFNVTRNDARAYVCGIQ
NSVSANRSDPVTLDVLYGPDTPIISPPDSSYLSGANLNLSCHSASNPSPQYSWRINGIPQQH
TQVLFIAKITPNNNGTYACFVSNLATGRNNSIVKSITVSASGXXPXLSAXATVGIXIGVLXX
VALI

*Fig. 9*

*SEQ ID No 6*

KLTIESTPFNVAEGKEVLLLVHNLPQHLFGYSWYKGERVDGNRQIIGYVIGTQQATPGPAYS
GREIIYPNASLLIQNIIQNDTGFYTLHVIKSDLVNEEATGQFRVYPELPKPSISSNNSKPVE
DKDAVAFTCEPETQDATYLWWVNNQSLPVSPRLQLSNGNRTLTLFNVTRNDTASYKCETQNP
VSARRSDSVILNVLYGPDAPTISPLNTSYRSGENLNLSCHAASNPPAQYSWFVNGTFQQSTQ
ELFIPNITVNNSGSYTCQAHNSDTGLNRTTVTTITVYAEPPKPFITSNNSNPVEDEDAVALT
CEPEIQNTTYLWWVNNQSLPVSPRLQLSNDNRTLTLLSVTRNDVGPYECGIQNELSVDHSDP
VILNVLYGPDDPTISPSYTYYRPGVNLSLSCHAASNPPAQYSWLIDGNIQQHTQELFISNIT
EKNSGLYTCQANNSASGHSRTTVKTITVSAELPKPSISSNNSKPVEDKDAVAFTCEPEAQNT
TYLWWVNGQSLPVSPRLQLSNGNRTLTLFNVTRNDARAYVCGIQNSVSANRSDPVTLDVLYG
PDTPIISPPDSSYLSGANLNLSCHSASNPSPQYSWRINGIPQQHTQVLFIAKITPNNNGTYA
CFVSNLATGRNNSIVKSITVSASGTSPGLSAGATVGIMIGVLVGVALI

Fig. 10
SEQ ID No 7

KLTIESTPFNVAEGKEVLLLAHNLPQNRIGYSWYKGERVDGNSLIVGYVIGTQQATPGPAYS
GRETIYPNASLLIQNVTQNDTGFYTLQVIKSDLVNEEATGQFHVYPELPKPSISSNNSNPVE
DKDAVAFTCEPEVQNTTYLWWVNGQSLPVSPRLQLSNGNMTLTLLSVKRNDAGSYECEIQNP
ASANRSDPVTLNVLYGPDVPTISPSKANYRPGENLNLSCHAASNPPAQYSWFINGTFQQSTQ
ELFIPNITVNNSGSYMCQAHNSATGLNRTTVTMITVSGSAPVLSAVATVGITIGVLARVALI

*Fig. 11*
SEQ ID No 8

```
GFTPSGTTGT TKLTVTEECQ VRVGDLTVAK TRGQLTDAAP IGPVTVQALG  50
         N          S        T S KWK  G D  NSQ V    T
         F          P   A  G RFR  D G      TS       N
         C          K   S  N NLS  S N      LD       C
         S          G   N  A AVE  N         M       S
         V          D   K  K TYQ  L         G       G
         R          R      K KPF  V         F       A
         A          N      R RNG  T                 P
         I          H      H HQL  A
         L          Q      Q  M
         Y                 M  P
                           N
                           T
                           W

CDARQVALKA DTDNFEQGKF FLISDNKRDK LYVNIRPTDN SAWTTDNGVF 100
         G                              D V M        L   M   Y
         N                                S L        H   Y   V
         S                                H              F
         C                                              C
         P                                              W
         Q                                              Q
         Y                                              N
         H                                              E
         K                                              S
         R                                              I
         T                                              H

YKNDVGSWGG IIGIYVDGQQ TNTPPGNYTL TLTGGYWAK           139
         S          C   VTA P
         A          V   LWS S
         T          H   AEL
         R          Y   CV
         M          T
         V          M
         P          F
         N
         E
         Q
         G
         K
         H
```

```
GFTPSGTTGT TKLTVTEECQ VRVGDLTVAK TRGQLTDAAP IGPVTVQALG  50
         N          S  T S KWK  G D NSQ    V       T
         F          P  A G RFR  D G TS            N
         C          K  N L S    S N LD            C
         S          G  N A V E  S N M             S
         V          D  K T Y Q  N L G             G
         R          R  K K P F  V F              A
         A          N  R N G    T A               P
         I          H  H Q L    A
         L          Q  Q H
         Y             M P
                       N T
                       T
                       W

CDARQVALKA DTDNFEQGKF FLISDNKRDK LYVNIRPTDN SAWTTDNGVF 100
G                              D V M        L  M  Y
N                                S  L       H  Y  V
S                                                 F
C                                                 C
P                                                 W
Q                                                 Q
Y                                                 N
H                                                 E
K                                                 S
R                                                 H
T                                                 H

YKNDVGSWGG IIGIYVDGQQ TNTPPGNYTL TLTGGYWAK             139
         S           C  V TA  P
         A           V  L WS  S
         T           H  A EI
         R           Y  C V
         M           T
         V           M
         P           F
         N
         E
         Q
         G
         K
         H
```

Fig. 14

```
GFTPSGTTGT TKLTVTEECQ VRVGDLTVAK TRGQLTDAAP IGFVTVQALG 50
N          S  T S KWK  G D NSQ    V        T
F          P  A G RFR  D S TS      N
C          K  S N L S  S S LD      C
S          G  N A V E  N N M       S
V          D  K T Y Q    L G       G
R          R    K P F    V F       A
A          N    R N G    T         P
I          H    H Q L    A
L          Q    Q   H
Y               M   P
                    N
                    T
                    W

CDARQVALKA DTDNFEQGKF FLISDNKRDK LYVNIRPTDN SAWTDNGVF 100
G                                D V M     L  M Y
N                                S   L     Y  F V
S                                H         F
C                                          C
P                                          W
Q                                          Q
Y                                          N
H                                          E
K                                          S
R                                          H
T

YKNDVGSWGG IIGLYVDGQQ TNTPPGNYTL TLTGGYWAK                 139
S          C  VTA  P                      H
A          V  LWS  S
T          H  AEL
R          Y  CV
M          T
V          M
P          F
N
E
Q
G
K
H
```

EECQVRVGDLTVAKTRGQLTDAAPIGPVTVQALGCDARQVALKADTDNFEQGKFFLISDNKR
DKLYVNIRPMDNSAWTTDNGVFYKNDVGSWGGVIGVYADGQQTNTPPGNYTLTLTGGYWAKD
NKQGFTPSGTTGTTKLTVT

*Fig. 15*
*SEQ ID 12*

SEQUENCE LISTING

```
<160> NUMBER OF SEQ ID NOS: 19

<210> SEQ ID NO 1
<211> LENGTH: 139
<212> TYPE: PRT
<213> ORGANISM: Escherichia coli

<400> SEQUENCE: 1

Gly Phe Thr Pro Ser Gly Thr Thr Gly Thr Thr Lys Leu Thr Val Thr
1               5                   10                  15

Glu Glu Cys Gln Val Arg Val Gly Asp Leu Thr Val Ala Lys Thr Arg
            20                  25                  30

Gly Gln Leu Thr Asp Ala Ala Pro Ile Gly Pro Val Thr Val Gln Ala
        35                  40                  45

Leu Gly Cys Asp Ala Arg Gln Val Ala Leu Lys Ala Asp Thr Asp Asn
    50                  55                  60

Phe Glu Gln Gly Lys Phe Phe Leu Ile Ser Asp Asn Lys Arg Asp Lys
65                  70                  75                  80

Leu Tyr Val Asn Ile Arg Pro Thr Asp Asn Ser Ala Trp Thr Thr Asp
                85                  90                  95

Asn Gly Val Phe Tyr Lys Asn Asp Val Gly Ser Trp Gly Gly Ile Ile
            100                 105                 110
```

```
Gly Ile Tyr Val Asp Gly Gln Gln Thr Asn Thr Pro Gly Asn Tyr
            115                 120                 125

Thr Leu Thr Leu Thr Gly Gly Tyr Trp Ala Lys
        130                 135

<210> SEQ ID NO 2
<211> LENGTH: 139
<212> TYPE: PRT
<213> ORGANISM: Artificial sequence
<220> FEATURE:
<223> OTHER INFORMATION: adhesin consensus sequence as described in
      figure 3 Xaa may be any naturally occuring amino acid
<220> FEATURE:
<221> NAME/KEY: site
<222> LOCATION: (1)..(139)
<223> OTHER INFORMATION: adhesin consensus sequence as described in
      figure 3 Xaa may be any naturally occuring amino acid

<400> SEQUENCE: 2

Xaa Xaa Xaa Xaa Xaa Xaa Xaa Xaa Xaa Xaa Xaa Xaa Xaa Xaa Xaa
1               5                   10                  15

Glu Xaa Cys Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Cys Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Gly Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Tyr
        115                 120                 125

Thr Xaa Xaa Xaa Xaa Xaa Xaa Xaa Xaa Xaa
        130                 135

<210> SEQ ID NO 3
<211> LENGTH: 139
<212> TYPE: PRT
<213> ORGANISM: Artificial sequence
<220> FEATURE:
<223> OTHER INFORMATION: Consensus sequence
<220> FEATURE:
<221> NAME/KEY: site
<222> LOCATION: (1)..(139)
<223> OTHER INFORMATION: consensus sequence

<400> SEQUENCE: 3

Gly Phe Thr Pro Ser Gly Thr Thr Gly Thr Thr Lys Leu Thr Val Thr
1               5                   10                  15

Glu Glu Cys Gln Val Arg Val Gly Asp Leu Thr Val Ala Lys Thr Arg
                20                  25                  30

Gly Gln Leu Thr Asp Ala Ala Pro Ile Gly Pro Val Thr Val Gln Ala
        35                  40                  45

Leu Gly Cys Xaa Ala Arg Gln Val Ala Leu Lys Ala Asp Thr Asp Asn
    50                  55                  60

Phe Glu Gln Gly Lys Phe Phe Leu Ile Ser Asp Asn Arg Asp Lys
65                  70                  75                  80

Leu Tyr Val Asn Ile Arg Pro Xaa Asp Asn Ser Ala Trp Thr Thr Asp
```

```
                    85                  90                  95
Asn Gly Val Phe Tyr Lys Asn Asp Val Gly Ser Trp Gly Gly Xaa Ile
                100                 105                 110

Gly Ile Tyr Val Asp Gly Gln Gln Thr Asn Thr Pro Pro Gly Asn Tyr
            115                 120                 125

Thr Leu Thr Leu Thr Gly Gly Tyr Trp Ala Lys
        130                 135

<210> SEQ ID NO 4
<211> LENGTH: 139
<212> TYPE: PRT
<213> ORGANISM: Artificial sequence
<220> FEATURE:
<223> OTHER INFORMATION: consensus sequence
<220> FEATURE:
<221> NAME/KEY: site
<222> LOCATION: (1)..(139)
<223> OTHER INFORMATION: consensus sequence

<400> SEQUENCE: 4

Gly Phe Thr Pro Ser Gly Thr Thr Gly Thr Thr Lys Leu Thr Val Thr
1               5                   10                  15

Glu Glu Cys Gln Val Arg Val Gly Asp Leu Thr Val Ala Lys Thr Arg
            20                  25                  30

Gly Gln Leu Thr Asp Ala Ala Pro Ile Gly Pro Val Thr Val Gln Ala
        35                  40                  45

Leu Gly Cys Xaa Ala Arg Gln Val Ala Leu Lys Ala Asp Thr Asp Asn
    50                  55                  60

Phe Glu Gln Gly Lys Phe Phe Leu Ile Ser Asp Asn Arg Asp Lys
65                  70                  75                  80

Leu Tyr Val Asn Ile Arg Pro Xaa Asp Asn Ser Ala Trp Thr Thr Asp
                85                  90                  95

Asn Gly Val Phe Tyr Lys Asn Asp Val Gly Ser Trp Gly Gly Xaa Ile
                100                 105                 110

Gly Ile Tyr Val Asp Gly Gln Gln Thr Asn Thr Pro Pro Gly Asn Tyr
            115                 120                 125

Thr Leu Thr Leu Thr Gly Gly Tyr Trp Ala Lys
        130                 135

<210> SEQ ID NO 5
<211> LENGTH: 203
<212> TYPE: PRT
<213> ORGANISM: Artificial sequence
<220> FEATURE:
<223> OTHER INFORMATION: CAECAM consensus sequence
<220> FEATURE:
<221> NAME/KEY: site
<222> LOCATION: (1)..(203)
<223> OTHER INFORMATION: CEACAM consensus sequence as described in
      figure 7; Xaa can be any naturally occuring amino acid

<400> SEQUENCE: 5

Xaa Xaa Xaa Xaa Xaa Xaa Xaa Pro Xaa Xaa Xaa Ala Glu Gly Lys Xaa
1               5                   10                  15

Val Leu Leu Xaa Xaa Xaa Asn Xaa Xaa Xaa Xaa Xaa Xaa Tyr Xaa
            20                  25                  30

Trp Xaa Lys Gly Xaa Xaa Xaa Xaa Xaa Xaa Xaa Ile Xaa Gly Tyr
        35                  40                  45

Xaa Xaa Xaa Xaa Gln Xaa Xaa Xaa Pro Gly Xaa Ala Xaa Xaa Xaa Arg
    50                  55                  60
```

```
Glu Xaa Xaa Tyr Xaa Asn Xaa Xaa Leu Leu Xaa Xaa Asn Xaa Xaa Xaa
 65                  70                  75                  80

Xaa Asp Xaa Gly Xaa Tyr Thr Leu Xaa Xaa Ile Xaa Xaa Xaa Xaa
                 85                  90                  95

Xaa Xaa Xaa Xaa Thr Xaa Gln Xaa Xaa Val Xaa Xaa Xaa Xaa Xaa
            100                 105                 110

Pro Xaa Xaa Xaa Xaa Xaa Xaa Xaa Xaa Xaa Xaa Xaa Xaa Xaa
        115                 120                 125

Val Xaa Xaa Xaa Xaa Xaa Xaa Xaa Xaa Xaa Xaa Xaa Leu Xaa
    130                 135                 140

Xaa Xaa Xaa Xaa Xaa Ser Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Ala Xaa Xaa Xaa
                180                 185                 190

Xaa Xaa Xaa Xaa Xaa Xaa Xaa Xaa Tyr Xaa Xaa
            195                 200

<210> SEQ ID NO 6
<211> LENGTH: 686
<212> TYPE: PRT
<213> ORGANISM: Artificial sequence
<220> FEATURE:
<223> OTHER INFORMATION: consensus sequence
<220> FEATURE:
<221> NAME/KEY: site
<222> LOCATION: (1)..(686)
<223> OTHER INFORMATION: consensus sequence

<400> SEQUENCE: 6

Lys Leu Thr Ile Glu Ser Thr Pro Phe Asn Val Ala Glu Gly Lys Glu
  1               5                  10                  15

Val Leu Leu Leu Xaa His Asn Leu Pro Gln Xaa Xaa Xaa Gly Tyr Ser
                 20                  25                  30

Trp Tyr Lys Gly Glu Arg Val Asp Gly Asn Xaa Xaa Ile Xaa Gly Tyr
             35                  40                  45

Val Ile Gly Thr Gln Gln Ala Thr Pro Gly Pro Ala Tyr Ser Gly Arg
 50                  55                  60

Glu Xaa Ile Tyr Pro Asn Ala Ser Leu Leu Ile Gln Asn Xaa Xaa Gln
 65                  70                  75                  80

Asn Asp Thr Gly Phe Tyr Thr Leu Xaa Val Ile Lys Ser Asp Leu Val
                 85                  90                  95

Asn Glu Glu Ala Thr Gly Gln Phe Xaa Val Tyr Pro Glu Leu Pro Lys
            100                 105                 110

Pro Ser Ile Ser Ser Asn Ser Xaa Pro Val Glu Asp Lys Asp Ala
        115                 120                 125

Val Ala Phe Thr Cys Glu Pro Glu Xaa Gln Xaa Xaa Thr Tyr Leu Trp
    130                 135                 140

Trp Val Asn Xaa Gln Ser Leu Pro Val Ser Pro Arg Leu Gln Leu Ser
145                 150                 155                 160

Asn Gly Asn Xaa Thr Leu Thr Leu Xaa Xaa Val Xaa Arg Asn Asp Xaa
                165                 170                 175

Xaa Ser Tyr Xaa Cys Glu Xaa Gln Asn Pro Xaa Ser Ala Xaa Arg Ser
            180                 185                 190

Asp Xaa Val Xaa Leu Asn Val Leu Tyr Gly Pro Asp Xaa Pro Thr Ile
        195                 200                 205
```

```
Ser Pro Xaa Xaa Xaa Xaa Tyr Arg Xaa Gly Glu Asn Leu Asn Leu Ser
    210                 215                 220

Cys His Ala Ala Ser Asn Pro Pro Ala Gln Tyr Ser Trp Phe Xaa Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Xaa Cys Gln Ala His Asn Ser Xaa Thr
            260                 265                 270

Gly Leu Asn Arg Thr Thr Val Thr Xaa Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Ala His Asn Ser Ala Thr Gly Leu Asn Arg
                325                 330                 335

Thr Thr Val Thr Met Ile Thr Val Gln Ser Leu Pro Val Ser Pro Arg
            340                 345                 350

Leu Gln Leu Ser Asn Asp Asn Arg Thr Leu Thr Leu Leu Ser Val Thr
        355                 360                 365

Arg Asn Asp Val Gly Pro Tyr Glu Cys Gly Ile Gln Asn Glu Leu Ser
    370                 375                 380

Val Asp His Ser Asp Pro Val Ile Leu Asn Val Leu Tyr Gly Pro Asp
385                 390                 395                 400

Asp Pro Thr Ile Ser Pro Ser Tyr Thr Tyr Arg Pro Gly Val Asn
                405                 410                 415

Leu Ser Leu Ser Cys His Ala Ala Ser Asn Pro Pro Ala Gln Tyr Ser
            420                 425                 430

Trp Leu Ile Asp Gly Asn Ile Gln Gln His Thr Gln Glu Leu Phe Ile
        435                 440                 445

Ser Asn Ile Thr Glu Lys Asn Ser Gly Leu Tyr Thr Cys Gln Ala Asn
    450                 455                 460

Asn Ser Ala Ser Gly His Ser Arg Thr Thr Val Lys Thr Ile Thr Val
465                 470                 475                 480

Ser Ala Glu Leu Pro Lys Pro Ser Ile Ser Ser Asn Asn Ser Lys Pro
                485                 490                 495

Val Glu Asp Lys Asp Ala Val Ala Phe Thr Cys Glu Pro Glu Ala Gln
            500                 505                 510

Asn Thr Thr Tyr Leu Trp Trp Val Asn Gly Gln Ser Leu Pro Val Ser
        515                 520                 525

Pro Arg Leu Gln Leu Ser Asn Gly Asn Arg Thr Leu Thr Leu Phe Asn
    530                 535                 540

Val Thr Arg Asn Asp Ala Arg Ala Tyr Val Cys Gly Ile Gln Asn Ser
545                 550                 555                 560

Val Ser Ala Asn Arg Ser Asp Pro Val Thr Leu Asp Val Leu Tyr Gly
                565                 570                 575

Pro Asp Thr Pro Ile Ile Ser Pro Pro Asp Ser Ser Tyr Leu Ser Gly
            580                 585                 590

Ala Asn Leu Asn Leu Ser Cys His Ser Ala Ser Asn Pro Ser Pro Gln
        595                 600                 605

Tyr Ser Trp Arg Ile Asn Gly Ile Pro Gln Gln His Thr Gln Val Leu
    610                 615                 620
```

```
Phe Ile Ala Lys Ile Thr Pro Asn Asn Asn Gly Thr Tyr Ala Cys Phe
625                 630                 635                 640

Val Ser Asn Leu Ala Thr Gly Arg Asn Asn Ser Ile Val Lys Ser Ile
            645                 650                 655

Thr Val Ser Ala Ser Gly Xaa Xaa Pro Xaa Leu Ser Ala Xaa Ala Thr
        660                 665                 670

Val Gly Ile Xaa Ile Gly Val Leu Xaa Xaa Val Ala Leu Ile
            675                 680                 685

<210> SEQ ID NO 7
<211> LENGTH: 668
<212> TYPE: PRT
<213> ORGANISM: Escherichia coli
<220> FEATURE:
<221> NAME/KEY: site
<222> LOCATION: (1)..(668)
<223> OTHER INFORMATION: CEA receptor
<220> FEATURE:
<221> NAME/KEY: site
<222> LOCATION: (1)..(110)
<223> OTHER INFORMATION: binding site for adhesins

<400> SEQUENCE: 7

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270
```

```
Gly Leu Asn Arg Thr Thr Val Thr Thr Ile Thr Val Tyr Ala Glu Pro
            275                 280                 285

Pro Lys Pro Phe Ile Thr Ser Asn Asn Ser Asn Pro Val Glu Asp Glu
290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
            355                 360                 365

His Ser Asp Pro Val Ile Leu Asn Val Leu Tyr Gly Pro Asp Asp Pro
370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
            435                 440                 445

Ala Ser Gly His Ser Arg Thr Thr Val Lys Thr Ile Thr Val Ser Ala
            450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
                500                 505                 510

Leu Gln Leu Ser Asn Gly Asn Arg Thr Leu Thr Leu Phe Asn Val Thr
            515                 520                 525

Arg Asn Asp Ala Arg Ala Tyr Val Cys Gly Ile Gln Asn Ser Val Ser
530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
            595                 600                 605

Ala Lys Ile Thr Pro Asn Asn Asn Gly Thr Tyr Ala Cys Phe Val Ser
610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Gly Ala Thr Val Gly
                645                 650                 655

Ile Met Ile Gly Val Leu Val Gly Val Ala Leu Ile
            660                 665

<210> SEQ ID NO 8
<211> LENGTH: 310
<212> TYPE: PRT
```

```
<213> ORGANISM: Escherichia coli
<220> FEATURE:
<221> NAME/KEY: site
<222> LOCATION: (1)..(310)
<223> OTHER INFORMATION: NCA receptor
<220> FEATURE:
<221> NAME/KEY: site
<222> LOCATION: (1)..(110)
<223> OTHER INFORMATION: binding site for adhesins

<400> SEQUENCE: 8
```

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Val Pro Thr Ile
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Met Ile Thr Val Ser Gly Ser Ala
        275                 280                 285

Pro Val Leu Ser Ala Val Ala Thr Val Gly Ile Thr Ile Gly Val Leu
    290                 295                 300

Ala Arg Val Ala Leu Ile
305                 310

```
<210> SEQ ID NO 9
<211> LENGTH: 139
<212> TYPE: PRT
<213> ORGANISM: Artificial sequence
<220> FEATURE:
<223> OTHER INFORMATION: consensus sequence
```

```
<220> FEATURE:
<221> NAME/KEY: site
<222> LOCATION: (1)..(139)
<223> OTHER INFORMATION: Adhesin consensus sequence according figure 12;
      pos. 7 is Thr, Asn, Phe, Cys, Ser, Val, Arg, Ala, Ile, Leu or Tyr;
      pos.17 is Glu, Ser, Pro, Lys, Gly, Asp, Arg, Asn, His or Gln; pos.
      22 is Arg, Thr, Ala, Ser, Asn or Lys
<220> FEATURE:
<221> NAME/KEY: site
<222> LOCATION: (1)..(139)
<223> OTHER INFORMATION: pos. 25 is Asp, Ser, Gly, Asn, Ala, Thr, Lys,
      Arg, His, Gln or Met; pos. 27 is Thr, Lys, Arg, Leu, Val, Tyr,
      Phe, Asn or Gln, pos. 28 is Val, Trp or Phe; pos. 29 is Ala, Lys,
      Arg, Ser, Glu, Gln, Phe, Gly, Leu, His, Pro, Asn, Thr or Trp
<220> FEATURE:
<221> NAME/KEY: site
<222> LOCATION: (1)..(139)
<223> OTHER INFORMATION: pos.31 is Thr, Gly, Asp, Ser or Asn; pos.34 is
      Gln, Asp, Gly, Ser, Asn, Leu, Val, Thr or Ala; pos.37 is Asp or
      Asn; pos.38 is Ala, Ser, Thr or Leu; pos.39 is Ala, Gln, Ser, Asp,
      Met, Gly or Phe; pos.41 is Ile or Val
<220> FEATURE:
<221> NAME/KEY: site
<222> LOCATION: (1)..(139)
<223> OTHER INFORMATION: pos.47 is Gln, Thr, Asn, Cys, Ser, Gly, Ala,
      Pro; pos.52 is Asp, Gly, Asn, Ser, Cys, Pro, Gln, Tyr, His, Lys,
      Arg or Thr; pos.84 is Asn, Asp, Ser or His; pos.86 is Arg or Val;
      pos.88 is Thr, Met or Leu
<220> FEATURE:
<221> NAME/KEY: site
<222> LOCATION: (1)..(139)
<223> OTHER INFORMATION: pos.95 is Thr, Leu, Met, Tyr, Phe, Cys, Trp,
      Gln, Asn, Glu, Ser, Ile or His; pos.100 is Phe, Tyr or Val; pos.
      105 is Val, Ser, Ala, Thr, Arg, Met, Val, Pro, Asn, Glu, Gln, Gly,
      Lys or His; pos.111 is Ile, Cys, Val, His, Tyr, Thr, Met or Phe
<220> FEATURE:
<221> NAME/KEY: site
<222> LOCATION: (1)..(139)
<223> OTHER INFORMATION: pos.114 is Ile, Val, Leu, Ala or Cys; pos. 115
      is Tyr, Thr, Trp, Glu or Val; pos.116 is Val, Ala, Ser or Leu;
      pos.118 is Gly, Phe or Ser; Xaa for the remaining positions can be
      any naturally occuring amino acid

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Thr Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa
    130                 135

<210> SEQ ID NO 10
<211> LENGTH: 139
<212> TYPE: PRT
<213> ORGANISM: Artificial sequence
<220> FEATURE:
<223> OTHER INFORMATION: consensus sequence
```

```
<220> FEATURE:
<221> NAME/KEY: site
<222> LOCATION: (1)..(139)
<223> OTHER INFORMATION: Adhesin consensus sequence according figure 13;
      pos. 7 is Thr, Asn, Phe, Cys, Ser, Val, Arg, Ala, Ile, Leu or Tyr;
      pos.17 is Glu, Ser, Pro, Lys, Gly, Asp, Arg, Asn, His or Gln; pos.
      22 is Arg, Thr, Ala, Ser, Asn or Lys
<220> FEATURE:
<221> NAME/KEY: site
<222> LOCATION: (1)..(139)
<223> OTHER INFORMATION: pos. 25 is Asp, Ser, Gly, Asn, Ala, Thr, Lys,
      Arg, His, Gln or Met; pos. 27 is Thr, Lys, Arg, Leu, Val, Tyr,
      Phe, Asn or Gln, pos. 28 is Val, Trp or Phe; pos. 29 is Ala, Lys,
      Arg, Ser, Glu, Gln, Phe, Gly, Leu, His, Pro, Asn, Thr or Trp
<220> FEATURE:
<221> NAME/KEY: site
<222> LOCATION: (1)..(139)
<223> OTHER INFORMATION: pos.31 is Thr, Gly, Asp, Ser or Asn; pos.34 is
      Gln, Asp, Gly, Ser, Asn, Leu, Val, Thr or Ala; pos.37 is Asp or
      Asn; pos.38 is Ala, Ser, Thr or Leu; pos.39 is Ala, Gln, Ser, Asp,
      Met, Gly or Phe; pos.41 is Ile or Val
<220> FEATURE:
<221> NAME/KEY: site
<222> LOCATION: (1)..(139)
<223> OTHER INFORMATION: pos.47 is Gln, Thr, Asn, Cys, Ser, Gly, Ala,
      Pro; pos.52 is Asp, Gly, Asn, Ser, Cys, Pro, Gln, Tyr, His, Lys,
      Arg or Thr; pos.84 is Asn, Asp, Ser or His; pos.86 is Arg or Val;
      pos.88 is Thr, Met or Leu
<220> FEATURE:
<221> NAME/KEY: site
<222> LOCATION: (1)..(139)
<223> OTHER INFORMATION: pos.95 is Thr, Leu, Met, Tyr, Phe, Cys, Trp,
      Gln, Asn, Glu, Ser, Ile or His; pos.100 is Phe, Tyr or Val; pos.
      105 is Val, Ser, Ala, Thr, Arg, Met, Val, Pro, Asn, Glu, Gln, Gly,
      Lys or His; pos.111 is Ile, Cys, Val, His, Tyr, Thr, Met or Phe
<220> FEATURE:
<221> NAME/KEY: site
<222> LOCATION: (1)..(139)
<223> OTHER INFORMATION: pos.114 is Ile, Val, Leu, Ala or Cys; pos. 115
      is Tyr, Thr, Trp, Glu or Val; pos.116 is Val, Ala, Ser or Leu;
      pos.118 is Gly, Phe or Ser; Xaa for the remaining positions can be
      any naturally occuring amino acid

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Leu Xaa Xaa Xaa Xaa Xaa Xaa
            20                  25                  30

Xaa Xaa Xaa Xaa Xaa Xaa Xaa Xaa Xaa Gly Pro Val Xaa Xaa Xaa Xaa
        35                  40                  45

Leu Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Asp Xaa Ser Xaa Xaa Xaa Xaa Xaa
                85                  90                  95

Xaa Xaa Xaa Xaa Xaa Xaa Xaa Xaa Xaa Ser Trp Xaa Gly Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa
    130                 135

<210> SEQ ID NO 11
<211> LENGTH: 139
<212> TYPE: PRT
<213> ORGANISM: Artificial sequence
<220> FEATURE:
<223> OTHER INFORMATION: consensus sequence
```

-continued

```
<220> FEATURE:
<221> NAME/KEY: site
<222> LOCATION: (1)..(139)
<223> OTHER INFORMATION: Adhesin consensus sequence according figure 13;
      pos. 7 is Thr, Asn, Phe, Cys, Ser, Val, Arg, Ala, Ile, Leu or Tyr;
      pos.17 is Glu, Ser, Pro, Lys, Gly, Asp, Arg, Asn, His or Gln; pos.
      22 is Arg, Thr, Ala, Ser, Asn or Lys
<220> FEATURE:
<221> NAME/KEY: site
<222> LOCATION: (1)..(139)
<223> OTHER INFORMATION: pos. 25 is Asp, Ser, Gly, Asn, Ala, Thr, Lys,
      Arg, His, Gln or Met; pos. 27 is Thr, Lys, Arg, Leu, Val, Tyr,
      Phe, Asn or Gln, pos. 28 is Val, Trp or Phe; pos. 29 is Ala, Lys,
      Arg, Ser, Glu, Gln, Phe, Gly, Leu, His, Pro, Asn, Thr or Trp
<220> FEATURE:
<221> NAME/KEY: site
<222> LOCATION: (1)..(139)
<223> OTHER INFORMATION: pos.31 is Thr, Gly, Asp, Ser or Asn; pos.34 is
      Gln, Asp, Gly, Ser, Asn, Leu, Val, Thr or Ala; pos.37 is Asp or
      Asn; pos.38 is Ala, Ser, Thr or Leu; pos.39 is Ala, Gln, Ser, Asp,
      Met, Gly or Phe; pos.41 is Ile or Val
<220> FEATURE:
<221> NAME/KEY: site
<222> LOCATION: (1)..(139)
<223> OTHER INFORMATION: pos.47 is Gln, Thr, Asn, Cys, Ser, Gly, Ala,
      Pro; pos.52 is Asp, Gly, Asn, Ser, Cys, Pro, Gln, Tyr, His, Lys,
      Arg or Thr; pos.84 is Asn, Asp, Ser or His; pos.86 is Arg or Val;
      pos.88 is Thr, Met or Leu
<220> FEATURE:
<221> NAME/KEY: site
<222> LOCATION: (1)..(139)
<223> OTHER INFORMATION: pos.95 is Thr, Leu, Met, Tyr, Phe, Cys, Trp,
      Gln, Asn, Glu, Ser, Ile or His; pos.100 is Phe, Tyr or Val; pos.
      105 is Val, Ser, Ala, Thr, Arg, Met, Val, Pro, Asn, Glu, Gln, Gly,
      Lys or His; pos.111 is Ile, Cys, Val, His, Tyr, Thr, Met or Phe
<220> FEATURE:
<221> NAME/KEY: site
<222> LOCATION: (1)..(139)
<223> OTHER INFORMATION: pos.114 is Ile, Val, Leu, Ala or Cys; pos. 115
      is Tyr, Thr, Trp, Glu or Val; pos.116 is Val, Ala, Ser or Leu;
      pos.118 is Gly, Phe or Ser; Xaa for the remaining positions can be
      any naturally occuring amino acid

<400> SEQUENCE: 11

Xaa Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Leu Xaa Xaa Xaa Xaa Xaa
                20                  25                  30

Xaa Xaa Xaa Xaa Xaa Xaa Xaa Xaa Xaa Gly Pro Val Xaa Xaa Xaa
            35                  40                  45

Leu Xaa Cys Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Asp Xaa Ser Xaa Xaa Xaa Xaa
                    85                  90                  95

Xaa Xaa Xaa Xaa Xaa Xaa Xaa Xaa Xaa Gly Ser Trp Xaa Gly Xaa Xaa
            100                 105                 110

Xaa Xaa Xaa Xaa Xaa Xaa Xaa Xaa Xaa Xaa Xaa Xaa Xaa Tyr
        115                 120                 125

Thr Xaa Xaa Xaa Xaa Xaa Xaa Xaa Xaa Xaa Xaa
    130                 135

<210> SEQ ID NO 12
<211> LENGTH: 143
<212> TYPE: PRT
<213> ORGANISM: Artificial sequence
<220> FEATURE:
<223> OTHER INFORMATION: DraE adhesin carrying 5 mutations
```

```
<400> SEQUENCE: 12

Glu Glu Cys Gln Val Arg Val Gly Asp Leu Thr Val Ala Lys Thr Arg
1               5                   10                  15

Gly Gln Leu Thr Asp Ala Ala Pro Ile Gly Pro Val Thr Val Gln Ala
            20                  25                  30

Leu Gly Cys Asp Ala Arg Gln Val Ala Leu Lys Ala Asp Thr Asp Asn
        35                  40                  45

Phe Glu Gln Gly Lys Phe Phe Leu Ile Ser Asp Asn Lys Arg Asp Lys
    50                  55                  60

Leu Tyr Val Asn Ile Arg Pro Met Asp Asn Ser Ala Trp Thr Thr Asp
65                  70                  75                  80

Asn Gly Val Phe Tyr Lys Asn Asp Val Gly Ser Trp Gly Gly Val Ile
                85                  90                  95

Gly Val Tyr Ala Asp Gly Gln Gln Thr Asn Thr Pro Pro Gly Asn Tyr
            100                 105                 110

Thr Leu Thr Leu Thr Gly Gly Tyr Trp Ala Lys Asp Asn Lys Gln Gly
            115                 120                 125

Phe Thr Pro Ser Gly Thr Thr Gly Thr Thr Lys Leu Thr Val Thr
        130                 135                 140

<210> SEQ ID NO 13
<211> LENGTH: 27
<212> TYPE: PRT
<213> ORGANISM: Artificial Sequence
<220> FEATURE:
<223> OTHER INFORMATION: Position 1-27 of consensus sequence SEQ ID NO 2
<220> FEATURE:
<221> NAME/KEY: site
<222> LOCATION: (1)..(27)
<223> OTHER INFORMATION: Position 1-27 of consensus sequence ID NO 2;
      pos. 7 is Thr, Asn, Phe, Cys, Ser, Val, Arg, Ala, Ile, Leu or Tyr;
      pos.17 is Glu, Ser, Pro, Lys, Gly, Asp, Arg, Asn, His or Gln; pos.
      22 is Arg,Thr, Ala, Ser, Asn or Lys
<220> FEATURE:
<221> NAME/KEY: site
<222> LOCATION: (1)..(27)
<223> OTHER INFORMATION: pos. 25 is Asp, Swer, Gly, Asn, Ala, Thr, Lys,
      Arg, His, Gln or Met; pos. 27 is Thr, Lys, Arg, Leu, Val, Tyr,
      Phe, Asn or Gln; Xaa at other positions can be any naturally
      occuring amino acid

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Xaa Xaa
            20                  25

<210> SEQ ID NO 14
<211> LENGTH: 26
<212> TYPE: PRT
<213> ORGANISM: Artificial Sequence
<220> FEATURE:
<223> OTHER INFORMATION: Position 28-53 of consensus sequence SEQ ID NO
      2; pos.1 is Val, Trp or Phe; pos.2 is Ala, Lys, Arg, Ser, Glu,
      Gln, Phe, Gly, Leu, His, Pro, Asn, Thr or Trp; pos.4 is Thr, Gly,
      Asp, Ser or Asn; pos.7 is Gln, Asp, Gly, Ser, Asn, Leu, Val, Thr
      or Ala;
<220> FEATURE:
<221> NAME/KEY: site
<222> LOCATION: (1)..(26)
<223> OTHER INFORMATION: Position 28-53 of consensus sequence SEQ ID NO
      2; pos.1 is Val, Trp or Phe; pos.2 is Ala, Lys, Arg, Ser, Glu,
      Gln, Phe, Gly, Leu, His, Pro, Asn, Thr or Trp; pos.4 is Thr, Gly,
      Asp, Ser or Asn; pos.7 is Gln, Asp, Gly, Ser, Asn, Leu, Val, Thr
      or Ala;
```

```
<220> FEATURE:
<221> NAME/KEY: site
<222> LOCATION: (1)..(26)
<223> OTHER INFORMATION: pos.10 is Asp or Asn; pos.11 is Ala, Ser, Thr
      or Leu; pos.12 is Ala, Gln, Ser, Asp, Met, Gly or Phe; pos.14 is
      Ile or Val; pos.20 is Gln, Thr, Asn, Cys, Ser, Gly, Ala, Pro; pos.
      25 is Asp, Gly, Asn, Ser, Cys, Pro, Gln, Tyr, His, Lys, Arg or Thr
<220> FEATURE:
<221> NAME/KEY: site
<222> LOCATION: (1)..(26)
<223> OTHER INFORMATION: Xaa at other positions can be any naturally
      occuring amino acid

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Xaa Xaa
            20                  25

<210> SEQ ID NO 15
<211> LENGTH: 19
<212> TYPE: PRT
<213> ORGANISM: Artificial sequence
<220> FEATURE:
<223> OTHER INFORMATION: Position 74-92 of consensus sequence SEQ ID NO
      2
<220> FEATURE:
<221> NAME/KEY: site
<222> LOCATION: (1)..(19)
<223> OTHER INFORMATION: pos. 70-88 of consensus sequence SEQ ID NO 2;
      pos.15 is Asn, Asp, Ser or His; pos. 17 is Arg or Val; pos.19 is
      Thr, Met or Leu; Xaa at other positions can be any naturally
      occuring amino acid

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 16
<211> LENGTH: 25
<212> TYPE: PRT
<213> ORGANISM: Artificial sequence
<220> FEATURE:
<223> OTHER INFORMATION: Position 98-122 of consensus sequence SEQ ID NO
      2
<220> FEATURE:
<221> NAME/KEY: site
<222> LOCATION: (1)..(25)
<223> OTHER INFORMATION: pos. 89-113 of consensus sequence SEQ ID NO 2;
      pos.7 is Thr, Leu, Met, Tyr, Phe, Cys, Trp, Gln, Asn, Glu, Ser,
      Ile or His; pos.12 is Phe, Tyr or Val; pos.17 is Val, Ser, Ala,
      Thr, Arg, Met, Val, Pro, Asn, Glu, Gln, Gly, Lys or His
<220> FEATURE:
<221> NAME/KEY: site
<222> LOCATION: (1)..(25)
<223> OTHER INFORMATION: pos.23 is Ile, Cys, Val, His, Tyr, Thr, Met or
      Phe; Xaa at other positions can be any naturally occuring amino
      acid

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Gly Xaa Xaa Xaa Xaa Xaa Xaa Xaa
            20                  25

<210> SEQ ID NO 17
<211> LENGTH: 26
<212> TYPE: PRT
<213> ORGANISM: Artificial sequence
```

```
<220> FEATURE:
<223> OTHER INFORMATION: Position 129-154 of consensus sequence SEQ ID
      NO 2
<220> FEATURE:
<221> NAME/KEY: site
<222> LOCATION: (1)..(26)
<223> OTHER INFORMATION: pos. 114-139 of consensus sequence SEQ ID NO 2;
      pos. 1 is Ile, Val, Leu, Ala or Cys; pos.2 is Tyr, Thr, Trp, Glu
      or Val; pos.3 is Val, ala, Ser or Leu; pos.5 is Gly, Phe or Ser;
      Xaa at other positions can be any naturally occuring amino acid

<400> SEQUENCE: 17

Xaa Xaa Xaa Xaa Xaa Xaa Xaa Xaa Xaa Xaa Xaa Xaa Xaa Xaa Tyr Thr
1               5                   10                  15

Xaa Xaa Xaa Xaa Xaa Xaa Xaa Xaa Xaa Xaa
            20                  25

<210> SEQ ID NO 18
<211> LENGTH: 52
<212> TYPE: PRT
<213> ORGANISM: Artificial sequence
<220> FEATURE:
<223> OTHER INFORMATION: Position 1-52 of consensus sequence SEQ ID NO 5
<220> FEATURE:
<221> NAME/KEY: site
<222> LOCATION: (1)..(52)
<223> OTHER INFORMATION: pos. 1-52 of consensus sequence SEQ ID NO 10;
      pos. 7 is Thr, Asn, Phe, Cys, Ser, Val, Arg, Ala, Ile, Leu or Tyr;
      pos.17 is Glu, Ser, Pro, Lys, Gly, Asp, Arg, Asn, His or Gln; pos.
      22 is Arg, Thr, Ala, Ser, Asn or Lys
<220> FEATURE:
<221> NAME/KEY: site
<222> LOCATION: (1)..(52)
<223> OTHER INFORMATION: pos. 25 is Asp, Swer, Gly, Asn, Ala, Thr, Lys,
      Arg, His, Gln or Met; pos. 27 is Thr, Lys, Arg, Leu, Val, Tyr,
      Phe, Asn or Gln; pos.28 is Val, Trp or Phe; pos.29 is Ala, Lys,
      Arg, Ser, Glu, Gln, Phe, Gly, Leu, His, Pro, Asn, Thr or Trp;
<220> FEATURE:
<221> NAME/KEY: site
<222> LOCATION: (1)..(52)
<223> OTHER INFORMATION: pos.31 is Thr, Gly, Asp, Ser or Asn; pos.34 is
      Gln, Asp, Gly, Ser, Asn, Leu, Val, Thr or Ala; pos.37 is Asp or
      Asn; pos.38 is Ala, Ser, Thr or Leu; pos.39 is Ala, Gln, Ser, Asp,
      Met, Gly or Phe; pos.41 is Ile or Val
<220> FEATURE:
<221> NAME/KEY: site
<222> LOCATION: (1)..(52)
<223> OTHER INFORMATION: pos.47 is Gln, Thr, Asn, Cys, Ser, Gly, Ala,
      Pro; pos.52 is Asp, Gly, Asn, Ser, Cys, Pro, Gln, Tyr, His, Lys,
      Arg or Thr; Xaa at the remaining positions can be any naturally
      occuring amino acid

<400> SEQUENCE: 18

Xaa Xaa Xaa Xaa Xaa Xaa Xaa Pro Xaa Xaa Xaa Ala Glu Gly Lys Xaa
1               5                   10                  15

Val Leu Leu Xaa Xaa Xaa Asn Xaa Xaa Xaa Xaa Xaa Xaa Xaa Tyr Xaa
            20                  25                  30

Trp Xaa Lys Gly Xaa Xaa Xaa Xaa Xaa Xaa Xaa Xaa Ile Xaa Gly Tyr
        35                  40                  45

Xaa Xaa Xaa Xaa
    50

<210> SEQ ID NO 19
<211> LENGTH: 151
<212> TYPE: PRT
<213> ORGANISM: Artificial sequence
<220> FEATURE:
<223> OTHER INFORMATION: Position 54-203 of consensus sequence SEQ ID NO
      5
<220> FEATURE:
<221> NAME/KEY: site
```

-continued

```
<222> LOCATION: (1)..(151)
<223> OTHER INFORMATION: pos. 53-203 of consensus sequence SEQ ID NO 5

<400> SEQUENCE: 19

Gln Xaa Xaa Xaa Pro Gly Xaa Ala Xaa Xaa Xaa Arg Glu Xaa Xaa Tyr
1               5                   10                  15

Xaa Asn Xaa Xaa Leu Leu Xaa Xaa Asn Xaa Xaa Xaa Xaa Asp Xaa Gly
            20                  25                  30

Xaa Tyr Thr Leu Xaa Xaa Ile Xaa Xaa Xaa Xaa Xaa Xaa Xaa Xaa Xaa
        35                  40                  45

Thr Xaa Gln Xaa Xaa Val Xaa Xaa Xaa Xaa Xaa Xaa Pro Xaa Xaa Xaa
    50                  55                  60

Xaa Xaa Xaa Xaa Xaa Xaa Xaa Xaa Xaa Xaa Xaa Xaa Val Xaa Xaa Xaa
65                  70                  75                  80

Xaa Xaa Xaa Xaa Xaa Xaa Xaa Xaa Xaa Xaa Leu Xaa Xaa Xaa Xaa Xaa
                85                  90                  95

Xaa Ser Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Ala Xaa Xaa Xaa Xaa Xaa Xaa Xaa
    130                 135                 140

Xaa Xaa Xaa Xaa Tyr Xaa Xaa
145                 150
```

OPTIMIZED ADHESIN FRAGMENTS AND CORRESPONDING NANOPARTICLES

CROSS-REFERENCES TO RELATED APPLICATIONS

This application is the U.S. National Stage of International Application No. PCT/EP2008/004867, filed Jun. 17, 2008, which designated the United States and has been published as International Publication No. WO 2009/106102 A1 and which claims the priority of European Patent Application, Serial No. 08003845.8 filed Feb. 29, 2008, pursuant to 35 U.S.C. 119(a)-(d) the description of which is hereby incorporated by reference.

BACKGROUND OF THE INVENTION

The invention relates to optimized adhesins and nanoparticles to which said adhesins are bound. The invention furthermore relates to providing said nanoparticles by way of in vivo contrast agents, in particular for the diagnosis of bowel cancer.

For many diseases, a diagnosis which is both as early as possible and meaningful is of crucial importance for choosing as well as coordinating and performing the necessary medical measures. This is especially true for many kinds of tumors, for the determination and therapy of which (including possible sections) it is essential to discriminate between healthy and carcinogenic tissues. Accordingly, the recovery or even survival of a patient crucially depends on, whether and to what extent the physician in charge of treatment and/or surgery is able to distinguish different types of tissues.

To improve diagnosis and medical measures, contrast agents have been developed in the past which can help with making visible functions and structures in the body by imaging processes. These processes are used inter alia for specifically detecting cancer-associated cellular alterations.

WO 2007/057182 A3, for example, discloses fluorescent nanoparticles comprising at least three structures, namely an inorganic core which is coated with a passivation layer which in turn carries specific ligands. These ligands allow said nanoparticle to specifically bind to a target. Said target may especially be specific surface molecules of the target cells, for example tumor-associated antigens.

The nanoparticles with core and surrounding passivation layer, which are disclosed by this printed publication, have a small hydrodynamic diameter which preferably is between 5 and 15 nm. Nanoparticles of this size can be illuminated via the kidneys and therefore do not, or at most only in tolerable amounts, accumulate in the body. This is one of the important requirements for using nanoparticles for medical purposes.

Another requirement is the high specificity of the ligands bound to the nanoparticles recognizing the selected target structure in the body. Only high-specific recognition allows detection which is the main purpose of the medical use of a contrast agent. These highly specific ligands must at the same time be so small that they do not impede good distribution and penetration of the nanoparticles. Frequently employed specific ligands such as antibodies or Fab fragments are usually too large in order to meet this requirement.

The number of new cases of bowel cancer in industrialized countries has risen significantly over the last 30 years. With an annual incidence of new cases of 30-35 per 100 000 inhabitants, bowel cancer is one of the most common malignancies in central Europe and is responsible for about 15% of all cancer fatalities. The worldwide incidence is estimated to be a million new cases per year. Men are slightly more affected than women, especially with rectal carcinomas (sex ratio 60:40).

In Germany, bowel cancer is the second most common form of cancer, both with new cases and with cancer fatalities in men and women, with more than 20 000 people having died in 2005. The "Gesellschaft der epidemiologischen Krebsregister [Society of epidemiological cancer registers]" even assumes that there are nearly 30 000 fatalities per year.

Bowel cancer refers to any malignant tumors of the intestines. They may be carcinoids, especially in the appendix and the small intestine, leiomyosarcomas and gastrointestinal stromal tumors (GISTs) which derive from the smooth muscle and/or the connective tissue of the intestinal mucosa. However, these diseases are rather rare and represent only a small proportion of all bowel cancer cases. The by far largest proportion of all bowel cancer cases (more than 95%) is represented by adenocarcinoma of the cecum, colon or rectum, for which the generic term colorectal cancer is also used.

Bowel cancer, especially colorectal carcinomas, vary rarely cause symptoms initially and nearly always develop from initially benign intestinal polyps. The chances of curing by surgery and subsequent chemotherapy with a 5-year rate of survival of, on average, from 40 to 60% crucially depends on the stage at which the bowel cancer is diagnosed. Preventive care and also early diagnosis are therefore of particular importance. The latter would be possible by way of early detection of bowel cancer cells, in particular CRCs (colorectal cancer cells).

Detection of CRCs requires a target which is specific to said cells and, if possible, is overexpressed in the tumor. Members of the CEACAM family (CEA-related cell adhesion molecule; CEA=carcinoembryonic antigen) are reported as having upregulated expression in CRC cells. CEACAM family members are therefore particularly suitable as targets for CRC detection. They include especially CEA (CEACAM5) and NCA (CEACAM6).

The CEACAM family is a member of the Ig superfamily. Each family member is highly glycosylated and consists of an N-terminal Ig variable-like domain, downstream of which there are up to 6 IgC2 domains. CEACAM1, CEACAM3 and CEACAM4 are inserted via a carboxy terminal transmembrane domain and cytoplasmic domain in the cell membrane, whereas CEA (CEACAM5), CEACAM6 (NCA), CEACAM7 and CEACAM8 are anchored via glycosyiphosphatidylinositol (GPI) on the membrane. The N-terminal domain within this group has more than 90% similarity at the amino acid level.

CEA and NCA are present in the cylindrical epithelium and in the goblet cells in colon tissue. There they are located on the apical surface of mature enterocytes, that is in the glycocalyx/microvillus region. CEACAM act as intercellular adhesion molecules. This strictly apical localization of CEACAM in normal colon epithelial cells has been abandoned in adenocarcinoma cells—the proteins are thus expressed on the entire cell surface. Cellular organization and cellular polarity has been abolished in CRC cells, and thus, for example, CEA and/or NCA can be found located on the entire cell surface. CEA may be released, thereby entering the bloodstream and thus being detected as serum tumor marker.

Ligands which have been reported for these receptors are inter alia adhesins of the Dr family of E. coli bacteria (Afa/Dr adhesins, DrCEA subfamily). These adhesins are located on the bacterial surface, partly organized in the fimbriae, of diffusely adhering E. coli (DAEC) strains and mediate adhesion thereof to epithelial cells. Members of this family are AfaE-I, AfaE-III, AfaE-V, DraE and DaaE, for example.

The structural assembly genes coding for Afa/Dr adhesins have a similar organization. They consist of operons comprising at least 5 genes (A to E). Genes A to D here encode accessory genes, with gene D encoding an invasin. Gene E encodes the actual adhesin.

The gene clusters have highly conserved regions, for example the genes afaA, afaB, afaC, afaD and afaF, which have regulatory or chaperone function, for example. The structural, AfaE-encoding gene is very heterogeneous, resulting in antigenically different adhesins being produced.

*E. coli* bacteria that express these members of the Afa/Dr family of adhesins adhere to CHO cells expressing CEA (Berger et al., Molecular Microbiology, (2004) 52(4), pp. 963-983, "Differential recognition of members of the carcinoembryonic antigen family by Afa/Dr adhesins of diffusely adhering *Escherichia coli* (Afa/Dr DAEC)"). Furthermore, adhesins are also described in Alain L. Servin (Clinical Microbiology Reviews (April 2005) 18(2), pp. 264-292, "Pathogenesis of Afa/Dr Diffusely Adhering *Escherichia coli*").

However, these known adhesins are still unsatisfactory with regard to their affinity for CEA. It is therefore an object of the present invention to provide adhesins or adhesin fragments ("adhesin constructs") which have high affinity for CRC cells. For this purpose, they should have an improved affinity for CEA over the known wild-type adhesins, if possible.

SUMMARY OF THE INVENTION

It is moreover an aim of the present invention to provide adhesins and/or adhesin fragments which are suited to being bound as ligand to a nanoparticle which can be utilized for providing a contrast agent. Said nanoparticle should be useable preferably medically, particularly preferably as in vivo contrast agent.

This object is achieved by providing adhesins or adhesin fragments that have been modified by a mutation compared to the respective wild-type adhesin amino acid sequence, preferably the DraE wild-type sequence. The modification advantageously results in an improved affinity of the adhesins of the invention for members of the CEACAM family, in particular for CEA and/or NCA. The adhesins and adhesin fragments of the invention will also be referred to generically as "modified" or "optimized" adhesins hereinbelow.

The optimized adhesins comprise one or more of the following mutations (the numbering of the amino acid positions here is based on the DraE wild-type amino acid sequence; see also SEQ ID No. 1 of DraE, FIG. 1).

T7 (N, F, C, S, V, R, A, I, L, Y); E17 (S, P, K, G, D, R, N, H, Q); R22 (T, A, S, N, K); D25 (S, G, N, A, T, K, R, H, Q, M); T27 (K, R, L, V, Y, P, N, Q); V28 (W, F); A29 (K, R, S, E, Q, F, G, L, H, P, N, T, W); T31 (G, D, S, N); Q34 (D, G, S, N, L, V, T, A); D37N; A38 (S, T, L); A39 (Q, S, D, M, G, F); I141 (V); Q47 (T, N, C, S, G, A, P); D52 (G, N, S, C, P, Q, Y, H, K, R, T); N84 (D, S, H); R86V; T88 (M, L); T95 (L, M, Y, F, C, W, Q, N, E, S, I, H); F100 (Y, V); V105 (S, A, T, R, M, V, P, N, E, Q, G, K, H); I111 (C, V, H, Y, T, M, F); I114 (V, L, A, C); Y115 (T, W, E, V); V116 (A, S, L); G118 (P, S).

However, if T88M and/or N77K are/is present, the adhesin of the invention must have at least one other of the abovementioned mutations. This applies in particular to those mutations which are present in an adhesin of the DraE group.

Preferred mutations are V28W; V28F; A39Q; A39S; I41L; Q47S; Q47T; I85L; T95L; G118S and T123I.

For the purpose of the invention, "adhesin" refers in principle to any protein which can bind to the N-terminal domain of a receptor from the CEACAM family (also binding protein hereinbelow), in particular to CEA and/or NCA. They include adhesins of the "adhesin group", the "DraE group", and in particular the proteins DraE and AfaE-III. They also include proteins having the consensus sequences derived from said adhesins.

The adhesins according to the invention preferably have a sequence of 139 amino acids and a size of 17 kDa. However, they may also have an N-terminal and/or C-terminal deletion, as long as this does not result in a loss of the ability to bind to CEACAM, in particular to CEA and/or NCA. The C-terminal deletion should not exceed 5, 8 or else at most 10 amino acids, if possible. The N-terminal deletion can be up to 18 amino acids. However, any shorter deletions, for example of 5, 8 or 10 amino acids, are also possible. In one embodiment of the invention, the adhesins are therefore 111 amino acids in length.

The "adhesin group" consists of AfaE-5, DrbE-122, DraE, SM254, DaaE; AfaE-2, AfaE-1 and NfaE-111 (in this context, see also FIG. 2; alignment). According to the invention, they have a consensus sequence according to SEQ ID No. 2 (FIG. 3), and one or more of the abovementioned mutations.

The same applies to the "DraE group" which consists of the following proteins (in this context, see also FIG. 4, alignment): G2152, SM297, JJB30, SM437, SM249, SM246, SM245, SM54, G2171, G2166, G2106, G2102, G2097, G2096, DraE, G2099, G2100, SM252, JJB17, SM293, G2076, SM513, AFaE-III. They have a consensus according to SEQ ID. No. 3 (FIG. 5). In one embodiment, the invention accordingly relates to adhesins with SEQ. ID No. 3 having one or more of the abovementioned mutations.

Particular preference is given to adhesins having a consensus according to SEQ. ID No. 4 (FIG. 6). The latter is derived from the alignment of DraE and AfaE-III. Particular preference is given to DraE.

The adhesins of the invention bind to the N-terminal sequence of proteins of the CEACAM group, which preferably a consensus sequence according to SEQ ID No. 5 (FIG. 7). Members of this group are CEA (CEACAM 5), NCA (CEACAM 6), CEACAM1, 3, 4, 7 and 8 (see also FIG. 8). They bind preferably to the N-terminal sequence of proteins with SEQ ID No. 6, which is derived from the alignment of CEA and NCA (FIG. 9, the region which contains only CEA is underlined). In one embodiment, the proteins of the invention bind to the N-terminal domain of CEA (SEQ ID No. 7, FIG. 10) and NCA (SEQ ID. No. 8, FIG. 11).

In a preferred embodiment, the modified adhesins according to DraE (SEQ ID No. 1), which bind to CEA and/or NCA, having one of the abovementioned mutations. Consequently, preference is given to an adhesin having a consensus sequence according to SEQ. ID No. 9 (alignment FIG. 12), as follows:

$X_6$ T7(N, F, C, S, V, R, A, I, L, Y) $X_9$ E17 (S, P, K, G, D, R, N, H, Q) $X_4$ R22(T, A, S, N, K) $X_2$ D25(S, G, N, A, T, K, R, H, Q, M) X T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) X A39(Q, S, D, M, G, F) X I41(V) $X_5$ Q47(T, N, C, S, G, A, P) $X_4$ D52(G, N, S, C, P, Q, Y, H, K, R, T) $X_{31}$ N84(D, S, H) X R86V X T88(M, L) $X_6$ T95(L, M, Y, F, C, W, Q, N, E, S, I, H) $X_4$ F100(Y, V) $X_4$ V105(S, A, T, R, M, V, P, N, E, Q, G, K, H) $X_5$ I111(C, V, H, Y, T, M, F) $X_2$ I114(V, L, A, C) Y115(T, W, E, V) V116(A, S, L) X G118(P, S) $X_{21}$.

In a further embodiment, the adhesins, in particular from DraE, have a consensus sequence according to SEQ ID No. 10 (alignment, see FIG. 13):

$X_6$ T7(N, F, C, S, V, R, A, I, L, Y) $X_9$ E17 (S, P, K, G, D, R, N, H, Q) $X_4$ R22(T, A, S, N, K) $X_2$ D25(S, G, N, A, T, K, R, H, Q, M) L26 T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) X A39(Q, S, D, M, G, F) X I41(V) G42 P43 V44 $X_2$ Q47(T, N, C, S, G, A, P) X L49 $X_2$ D52(G, N, S, C, P, Q, Y, H, K, R, T) $X_{31}$ N84(D, S, H) X R86V X T88(M, L) D89 X S91 $X_3$ T95(L, M, Y, F, C, W, Q, N, E, S, I, H) $X_4$ F100(Y, V) $X_4$ V105(S, A, T, R, M, V, P, N, E, Q, G, K, H) X S107 W108 X G110 I111(C, V, H, Y, T, M, F) $X_2$ I114(V, L, A, C) Y115(T, W, E, V) V116(A, S, L) X G118(P, S) $X_{21}$.

In another embodiment, the adhesins, in particular from DraE, have the following consensus sequence (SEQ ID No. 11, FIG. 14):

$X_6$ T7(N, F, C, S, V, R, A, I, L, Y) $X_9$ E17 (S, P, K, G, D, R, N, H, Q) X C19 $X_2$ R22(T, A, S, N, K) $X_2$ D25(S, G, N, A, T, K, R, H, Q, M) L26 T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) A39(Q, S, D, M, G, F) X I41(V) G42 P43 V44 $X_2$ Q47(T, N, C, S, G, A, P) X L49 X C51 D52(G, N, S, C, P, Q, Y, H, K, R, T) $X_{31}$ N84(D, S, H) X R86V X T88(M, L) D89 X S91 $X_3$ T95(L, M, Y, F, C, W, Q, N, E, S, I, H) $X_4$ F100(Y, V) $X_4$ V105(S, A, T, R, M, V, P, N, E, Q, G, K, H) G106 S107 W108 X G110 I111(C, V, H, Y, T, M, F) $X_2$ I114(V, L, A, C) Y115(T, W, E, V) V116(A, S, L) X G118(P, S) $X_9$ Y128 T129 $X_{10}$.

The consensus sequences specified, SEQ ID No. 9, 10 and 11, are based on the numbering according to SEQ ID. No 1. Here too, the abovementioned deletions may be at the N terminus and/or C terminus, as long as this does not render impossible binding of the adhesin to a CEACAM member, in particular CEA and/or NCA.

In a particular embodiment, preference is given to an adhesin according to SEQ ID No. 1, which comprises the following mutations, namely N77K, T88M, I111V, I114V and V116A (also "Fünfach-Mutante" [quintuple mutant], FM, hereinbelow; SEQ ID No. 12, FIG. 15).

A person skilled in the art is in principle familiar with the preparation of adhesin monomers. In the recombinant protein AfaE-III-dsc, for example, the N-terminal crosslinking section G is cloned to the C terminus and a linker is introduced between F and G. Section G then folds back across the linker and binds to the now N-terminal section A1 and thereby stabilizes the monomeric structure. This monomeric structure of AfaE-III-dsc can then be detected by gel filtrations (see FIG. 1C, from Anderson et al., 2004).

Piatek et al. (Infection and Immunity (2005) 73(1) pp. 135-145, "Molecular Aspects of Biogenesis of *Escherichia coli* Dr Fimbriae: Characterization of DraB-DraE-Complexes") describe another possibility of generating monomeric adhesins. They remove a different number of amino acids from the N-terminus of adhesin and thus obtain monomeric proteins (see FIG. 2, from Piatek et al., 2005). These known principles are basically also applicable to the adhesins modified according to the invention.

To obtain a modified adhesin, a wild-type adhesin may be subjected to mutagenesis, for example to an oligonucleotide-based, site-specific mutagenesis (e.g. EP1777292 A1).

In a preferred embodiment, the adhesins of the invention may be prepared by employing an adhesin construct having a reduced affinity for DAF (decay accelerating factor, CD55) as template for further mutagenesis (mutageneses). An example of this is the N77K mutation (van Loy et al., Molecular Microbiology (2002) 45(2), pp. 439-452, "Identification of amino acids in Dr adhesin required for binding to decay-accelerating factor").

The libraries produced by said mutagenesis may be transformed together with the target into yeast, and the reporter gene readout may be detected (in this context, see also the exemplary embodiments below). This enables the adhesins of the invention having an improved affinity for CEA and/or NCA to be identified.

The adhesins of the invention may be bound to nanoparticles. The latter may preferably be employed as in vivo contrast agents for detecting CRC cells. WO 2007/057182 A3 discloses advantageous nanoparticles, and reference is made to the entire contents thereof for purposes of disclosure of preparing and using said nanoparticles. Said nanoparticles are in particular those whose hydrodynamic diameter does not exceed 15 nm and which are non-inert in biological systems.

The nanoparticles of the invention comprise at least three structures, namely an inorganic core which is coated by a passivation layer which then in turn carries specific ligands, wherein said specific ligands may also be part of the passivation layer. Said ligands result in the nanoparticle binding specifically to the target of the biological system.

In preferred nanoparticles, the inorganic core including the passivation layer surrounding it has a hydrodynamic diameter of no more than 15, if possible, preferably no more than 10 nm. Particular preference is given to hydrodynamic diameters of no more than 8 nm or no more than 5 nm. This applies especially to spherical nanoparticles. Nanoparticles of this size can be illuminated via the kidneys and therefore do not accumulate, or at most accumulate in tolerable quantities, in the body. This makes in vivo application possible. This applies in particular to nanoparticles having a hydrodynamic diameter of no more than 5 nm.

In an alternative embodiment, the nanoparticles may also be rod-like. In this development, it is advantageous if the diameter of the rod does not exceed the abovementioned limit of 15 nm. Here too, preference is given to diameters in the range of 5, 8 or 10 nm to facilitate elimination from the body. Thus, for example, the nanoparticles employable according to the invention may have length/breadth dimensions of 8×15 nm.

The nanoparticles employable according to the invention preferably have maximum emission at a wavelength between 600 and 700 nm, for example between 620 and 660, particularly preferably at about 625 nm or 655 nm. Said emission is readily visible to the human eye, and such nanoparticles can therefore be used directly as contrast agents for medical interventions. Consequently, auxiliary optical instruments may in some circumstances be dispensed with.

In an alternative embodiment, nanoparticles exceeding the abovementioned hydrodynamic diameters may be employed according to the invention, as long as the particles are guaranteed to be non-inert in vivo. The latter is the precondition for said particles to be biodegradable and, as a result, the metals (e.g. Cd) which are bound therein as particulates initially, to be converted into the ionic form. The degradation products can be illuminated via the kidneys.

Inorganic nanoparticles having a passivation layer containing an imidazole component are indeed non-inert in vivo, as has been demonstrated previously, but they are degraded under these conditions. Said nanoparticles therefore satisfy the criterion of biodegradability and of renal passage of the degradation products, which is particularly relevant for in vivo application. This was a surprise finding because the passivation layer serves especially also to increase the chemical and/or physical stability of the nanoparticles (in this context, see also the additional comments below). Thus, the relationship between on the one hand the stability of the nanoparticles which is required for good diagnostics, and on the other hand biodegradability which is required for renal passage of "large" particles is suitable for use as in vivo contrast agent.

The main task of the passivation layer is to increase fluorescence intensity and chemical and physical stability of the inorganic core. The inorganic cores coated by the passivation layer are characterized by a quantum yield of at least 10%, advantageously at least 30, 50 or even 70%. Quantum yield here means the ratio of the amount of the light emitted by a sample to the amount of light absorbed by the sample. Advantageously, the passivation layer has a thickness of no more than 1 nm. In this case, the diameter of the passivated core increased by no more than 2 nm.

Advantageously, the nanoparticles are in each case also provided with modifiers, in particular for improving compatibility with the biological environment. Preferably, the increase in the hydrodynamic radius due to the use of modifiers does not exceed 2 nm. In particular cases, the thickness of the passivation layer and the modifiers also depends on the relationships of the two structures among each other and in relation to the inorganic core.

The nanoparticles of the invention, if restricted in size as mentioned above, are particularly suitable for the use as diagnostic agent in a living patient. Thus, the size reduction increases the rate of diffusion and depth of penetration into the tissue. This allows the nanoparticles to spread evenly and rapidly in the biological environment and also penetration as far as possible of a tissue (for example a tumor) after local administration. The nanoparticles of the invention likewise allow systemic administration which may also be carried out by way of injection. However, local administration, for example topical application or intra- or peritumoral administration for the treatment of tumors is also possible.

Particularly advantageous embodiments of the invention comprising the nanoparticles coupled to the modified adhesins have a hydrodynamic diameter of no more than 8, particularly preferably of no more than 4 nm. Nanoparticles of this order of magnitude may already be illuminated via the kidneys and therefore do not accumulate, or accumulate to a distinctly lesser extent, in the body. As a result, the nanoparticles of the invention reduce considerably the problem of long-term toxicity probably associated with the known quantum dots.

The nanoparticles advantageously emit a fluorescent spectrum between 600 and 700 nm, particularly preferably with maximum emission between 600 and 660 nm, particularly preferably between 620 and 660 nm. Said emission spectrum has the advantage of very high tissue transmission owing to only low absorption by hemoglobin and other light-absorbing substances in a living system (including water). Light of these wavelengths can still be sensed by the human eye and therefore enables the physician in charge of the treatment to identify the labeled tissue without any further complicated technical detection aids (e.g. CCD cameras). This is particularly advantageous when using the nanoparticles of the invention as contrast agents during surgical intervention for identifying CEA- and/or NCA-expressing cells, in particular for discriminating carcinogenic and healthy tissues.

In one embodiment, the preferably employable nanoparticles are known nanoparticles having a core of, for example, CdSe, CdS or CdTe, as described, for example, in US 2004/0247861 with reference to scientific publications. This printed publication also makes reference to documents regarding the preparation of the core materials, for example to U.S. Pat. No. 6,179,912. Reference is made to the entire contents of these documents regarding the disclosure of the properties of these known nanoparticles and the preparation thereof. A method of preparing nanoparticles is furthermore also disclosed in U.S. Pat. No. 7,147,712 B2 to which reference is also made for purposes of disclosure.

Particularly advantageously, the inorganic core of the nanoparticles essentially consists of semiconductors. These cores emit light of various colors, depending on their individual size and/or composition, but all of them absorb over a broad band within the same range of the light spectrum (UV to VIS range). Due to the high Stokes shift, excitation and emission spectra are far apart, enabling simple and simultaneous excitation of various nanoparticles. They have narrow and symmetric emission spectra which overlap only slightly or not at all. Other beneficial properties which are of great importance particularly for improved depth of filtration and in vivo labeling are the high quantum yield of up to 80% and high photostability.

Preferred nanoparticles have been disclosed, for example, in WO 2005/001889. Accordingly, they comprise an inorganic core made of an alloy of at least two semiconductors which either are distributed homogeneously or for which there is in each case a concentration gradient within the alloy. In respect of the disclosure of the nature and preparation of said nanoparticles, reference is made to WO 2005/001889 cited above. The cores may deviate in their size by in each case 5%.

Accordingly, the inorganic core of the nanoparticles may comprise an alloy of at least two semiconductors, wherein the core has a homogeneous composition and is characterized by a "band-gap energy" which is nonlinear to the molar ratio of the two semiconductors.

Alternatively, the core may be non-homogeneous, with the concentration of the first semiconductor gradually increasing, starting from the center of the core to the surface of the core, and the concentration of the second semiconductor gradually decreasing from the center of the core to its surface.

For both cores, at least one of the semiconductors is a group II-group VI semiconductor or a group III-group V semiconductor (the definition of groups corresponds to the groups of the Periodic Table of the Elements). For example, the alloy may be selected from the group of the following alloys: CdSeTe, CdSSe, CdSTe, ZnSeTe, ZnCdTe, CdHgS, CdHgTe, InGaAs, InGaP, GaAlAs, InGaN. These cores may moreover carry a coating of inorganic material such as, for example, semiconductors (e.g. ZnS). This additional layer is known to the skilled worker as "capping" or "shell".

Group II-group VI and group III-group V semiconductors are generally known and include, for example, $CdS_{1-x}Se_x$, $CdS_{1-x}Te_x$, $CdSe_{1-x}Te_x$, $ZnSe_{1-x}Te_x$, $Zn_{1-x}Cd_xTe$, $Cd_{1-x}Hg_xS$, $Cd_{1-x}Hg_xTe$, $In_{1-x}Ga_xAs$, $Ga_{1-x}Al_xAs$ and $In_{1-x}Ga_xP$. Preference is given to using the semiconductors $CdSe_{1-x}Te_x$, $CdS_{1-x}Te_x$, $ZnSe_{1-x}Te_x$, $Zn_{1-x}Cd_xTe$, $Cd_{1-x}Hg_xS$, $Cd_{1-x}Hg_xTe$, $In_{1-x}Ga_xAs$, $In_{1-x}Ga_xP$, where x is a fraction from 0 to 1.

The molar ratio of the semiconductors may be any molar ratio. However, if the alloy comprises CdSSe, preference is given to an alloy having the molecular formula $CdS_{1-x}Se_x$. If the alloy comprises CdSTe, preference is given to an alloy having the molecular formula $CdS_{1-x}Te_x$. If the alloy comprises ZnSeTe, preference is given to an alloy having the molecular formula $ZnSe_{1-x}Te_x$. If the alloy comprises ZnCdTe, preference is given to an alloy having the molecular formula of CdTe alone. In each of these cases, x is a fraction between 0 and 1.

These preferred inorganic cores of the nanoparticles may be prepared using the following steps: (i) preparation of a first solution under conditions which enable nanocrystals to form, (ii) preparation of a second solution which comprises a precursor of the semiconductors with a molar ratio under a condition which does not enable nanocrystals to form, (iii) addition of the second solution to the first solution which enables nanoparticles to form, and (iv) alteration of the conditions, which stops growth and formation of the nanocrystals. The method of preparing the cores is illustrated in WO 2005/001889 to which reference is made in respect of the disclosure of the preparation of this preferred embodiment of the inorganic core of the nanoparticles of the invention.

In an alternative embodiment, the inorganic core may essentially consist of a noble metal cluster which preferably comprises 2 and 27 noble metal atoms. In a preferred embodiment, the noble metal was selected from a group consisting of gold, silver, copper, platinum, palladium, osmium, iridium, ruthenium and rhodium. The cluster may have varying charges.

These cores have the advantage that they can be detected readily as individual "nanodots", using a weak mercury lamp excitation, owing to their strong absorbance and emission. The nanoparticles of the invention containing these cores can advantageously be used as fluorescent individual molecule label and mass label.

The term "noble metal" to a group of elements selected from a group consisting of gold, silver and copper, and the platinum group metals (PGM), platinum, palladium, osmium, iridium, ruthenium and rhodium. In preferred embodiments of the present invention, the noble metals are selected from the group consisting of gold, silver and copper. In a particularly preferred embodiment, the noble metal is silver or gold.

The term "cluster" relates to a compound of 2-27 atoms of a metal. Clusters are known inter alia from the fields of chemical catalysis, ceramics, semiconductor technology and material sciences. A person skilled in the art is therefore familiar with their preparation. WO 2004/003558 describes inter alia the preparation of noble metal clusters and in addition contains extensive further references on this subject. More specifically, it discloses the preparation of noble metal nanoclusters associated with organic molecules. The term association here means any form of binding, independently of the chemical or physical nature of the binding (thus, for example, covalent, noncovalent, electrostatic or van der Waals binding). Reference is made to WO 2004/003558 in respect of preparation of the nanoclusters as core of the nanoparticles of the invention.

The nanoparticles preferably employable according to the invention have a passivation layer which increases fluorescence intensity and improves the chemical and physical stability of the inorganic core. As a result, the nanoparticles emit light preferably with a quantum yield of more than 10%, preferably of more than 50%.

Said nanoparticles preferably have a storage stability of at least 12 months in an aqueous environment at 4° C. and are, if possible, stable across a pH range from pH 5 to pH 10, preferably from pH 7 to pH 10, i.e. they exhibit deviations of less than 50% in respect of their specific spectral characteristics such as quantum yield, position of maximum emission, half-width of the emission spectrum. Preferred particles exhibit deviations of less than 10% in respect of these specific spectral characteristics.

The nanoparticles employable according to another embodiment of the invention exhibit essentially a constancy/stability of the properties of the core (including the passivation layer surrounding it) also under biological (i.e. physiological) conditions or in vivo over a period of at least three days. Preferred particles exhibit a constancy/stability of this kind for a period of from 7 to 14 days, wherein by way of stability retaining at least 50% of the one constancy of the properties. This information refers especially to the stability of the nanoparticles in the actual target organ. It is noteworthy that the stability of the nanoparticles in organs which have primarily catabolic function may be distinctly less stable (for example in the liver). This may even be expressly desirable.

Although the nanoparticles are stable in the above sense, they are nevertheless fundamentally degradable in vivo and consequently are non-inert. In this sense, "non-inert" means that at least 50% of the nanoparticles have already been degraded after 12 weeks or more post-administration. Preference is given to at least 50% degradation being detectable already after 8, 6 or 4 weeks. Detection of the particles remaining in the body includes detection in body organs and in the plasma for this purpose. Accordingly, "inert" means that more than 50%, even up to nearly 100%, of the particles are still detectable in the body of the patient after 4 weeks post-administration.

Degradability of the nanoparticles can be detected by assays which are known to the skilled worker, namely, for example, by inductively coupled plasma mass spectrometry (ICP-MS), which assays may also be supplemented by fluorescence spectrometry measurements, if the samples are suitable (see also hereinbelow for this).

The passivation layer contains at least one compound which is capable of coordinating metal atoms or metal ions, for example zinc ions, mercury ions or cadmium ions. This compound may be a Lewis base or a cyclic or linear unsaturated compound with resonant electrons. By way of a cyclic unsaturated compound, it may also be a heterocycle or a heteroaromatic. In a preferred embodiment, the unsaturated or conjugated group is in a terminal position based on the structure of the molecule. The passivation layer may furthermore have a crosslinker, or the cyclic or linear unsaturated compound may also act as a crosslinker. The crosslinker may be basic.

The coordination compounds containing metal atoms or metal ions may functionally bind to fluorescent inorganic cores by means of chelation, coordination or electron donor properties of Lewis bases and have correspondingly conjugated moieties/groups. Said molecules may moreover contain moieties which impart solubility or wettability to the cores coated with them in aqueous solutions.

Said molecules or compounds may include a homogeneous or heterogeneous (heterocyclic) ring system containing one, two or more bonded (or also fused) rings. Preferred examples of heteroaromatic systems are thiazoles, thiazole derivatives, oxazoles, oxazole derivates, pyrroles, pyrrole derivatives including doped or undoped polypyrrole oligomers, thiophenes, thiophene derivatives including doped and undoped polythiophenes, furans, furan derivatives, pyridine and pyridine derivatives, pyrimidine and its derivatives, pyrazines, pyrazine derivatives, triazine and triazine derivatives, triazoles, triazole derivatives, phthalocyanines and phthalocyanine derivatives, porphyrin and porphyrin derivatives. Said compounds may include unsaturated (olefinic) hydrocarbons or amines, phosphorous derivatives or oxygen derivatives thereof which may include acetylene, propyne and allene, but without being limited thereto. Preference should be given to the molecule having sufficient p- or pi-electron density in order to participate in the formation of adducts or resonance on the surface of the semiconductor core.

Said heteroaromatic compound is preferably an imidazole component. Preference is furthermore given to adding a phosphine compound, preferably an alkylphosphine compound, as crosslinker.

The term "imidazole component" means for the purposes of the present description a heterocyclic or heteroaromatic molecule which contains at least one imidazole group (including imidazole derivatives) and which is available for binding of the inorganic core or the passivation layer having a metal such as cadmium, zinc, gallium, or a metal cation or a substrate containing such a cation. In this connection, preferably at least one imidazole group should be at a terminal position based on the structure of the molecule. The imidazole component in its functional form binds via the ring which contains delocalized molecular orbitals to the fluorescent nanocrystal. Usually, the nitrogen atoms of the imidazole ring serve as coordination ligands to functionally bind a metal ion such as cadmium or zinc.

In one embodiment, the imidazole component comprises reactive functional groups such as one or two amino acid(s), for example histidine, carnosine, anserine, baleine, homocarnosine, histidylphenylalanine, cyclo-histidylphenylalanine, 5-amino-4-imidazole-carboxamide, histidylleucine, 2-mercaptoimidazole, boc-histidine, hydrazide, histinol, 1-methylhistidine, 3-methylhistidine, imidazolysine, imidazole-containing ornithine (e.g. 5-methylimidazole), imidazole-containing alanine (e.g. (beta)-(2-imidazolyl)-L-(alpha) alanine), carzinine, histamine. These histidine-based molecules or imidazole-containing amino acids may be synthesized by generally known methods.

The term "phosphine" means for the purpose of the invention a molecule which has at least one phosphine group (including their derivatives) for binding or chelating a nonmetal such as Se, S or other nonmetals or substrates containing such atoms, and which provides at least one functional group (for example hydroxyl-, amino-, thiol-, carboxyl-, carboxamide- etc.) for reaction with neighboring molecules.

Preferably, at least one phosphine group should be located at a terminal position based on the structure of the molecule. The phosphine moieties serve as coordination ligands to bind in its functional form with a fluorescent core or a compound from the shielding layer a nonmetal or ion such as Se or S.

In a preferred embodiment, the phosphine-containing compound includes one, two or more phosphine groups coupled to one another (e.g. in polymeric form) which may include hydroxymethylphosphine compounds or the like but without being limited thereto. Phosphine-containing compounds may be synthesized by generally known methods. Furthermore, alkylphosphine-containing compounds are known to possibly also have one or more additional functional groups (e.g. hydroxyl-, amino-, thiol-, carboxyl-, carboxamide-, etc.). Examples of derivatives are hydroxymethylphosphine derivatives, amides or esters, as long as said derivatization is compatible with the functions described herein of phosphine as coating.

Particular preference is given to tris(hydroxymethyl)phosphine and β-[tris(hydroxy-methyl)phosphino]propanoic acid for coating the fluorescent inorganic cores of the nanoparticles of the invention. Crosslinked phosphine-containing compounds are well known to additionally be able to functionally bind to metal atoms and/or ions such as Zn or Cd. Isocyanates or alkylcyanoacrylates functionalized in this respect may furthermore be useful as crosslinkers for ligands and the formation of adducts with fluorescent cores. Said crosslinkers may also be basic.

The passivating effect of the passivation layer present according to the invention is based on the shielding of surface cadmium or zinc atoms or the like by complex formation with the heteroaromatic or heterocycle (preferably with the imidazole component), and on the shielding of the counteratoms (Se or S or the like) via complex formation with the phosphine-containing compounds.

The passivation layer of the nanoparticles of the invention has been disclosed in US 2004/0247861 A1. This laid-open application describes the preparation of inorganic cores coated with the passivation layer, for example of quantum dots. Reference is therefore made to US 2004/0247861 for purposes of disclosure of the preparation of the passivation layer employed according to the invention and of the inorganic cores coated therewith.

The molecules of the passivation layer may furthermore have or carry chemical groups in order to bind and crosslink target molecules and cells (specific ligands). In the presence of appropriately suitable reagents such as $ZnSO_4$ and $Na_2S$, said molecules or compounds may form a passivation layer with the molecules on the fluorescent core ("capping" or "shell"). These reagents may also functionally bind to atoms or ions on the surface of the fluorescent nanocrystal and, as a result, this additional passivation layer may also be formed directly on the surface of the core.

In an advantageous embodiment, the nanoparticles of the invention may additionally have modifiers which may consist of organic and/or inorganic moieties. They are used for improving compatibility, efficacy and/or solubility of the nanoparticles in a liquid or a suspension medium, in particular in the physiological environment. This surface modification is especially advantageous for achieving very low unspecific adsorption and increased compatibility in biological systems, in particular in the human body.

One possibility is to modify the surface with polyethylene glycol (PEG) which has already been approved for particular medical applications, in particular in low molecular weight forms for the nanoparticle to maintain a small overall size. Thereby both biocompatibility and blood circulation time of the nanoparticles and also the efficiency of uptake into cells may be increased. Combining a low molecular weight PEG layer with other substances such as vitamins, for example folic acid, may achieve a lower uptake of said nanoparticles into macrophages because protein adsorption to the nanoparticles, which is reduced thereby, makes recognition of said nanoparticles by the immune system more difficult.

Another possible advantageous surface modification by using modifiers is the coating with monosaccharides, di- or trisaccharides at up to low molecular weight polysaccharides composed of one type of monosaccharide or different monosaccharides. One possible type of development is a modification with polyglucose, for example, in which dextran can be used which has been proved medically as blood substitute. It exhibits good biocompatibility/tolerance. Another embodiment is the use of stereoisomeric forms (D-/L-) of saccharides in order to counteract possible degradation.

Another embodiment is the use of biologically compatible hydrophilic vitamins as modifiers, for example thiamine, riboflavin, niacin, pyridoxine, cobalamin, panthothenic acid, ascorbic acid and folic acid. Thus, for example, folic acid can lead to a preferred binding of nanoparticles to cancer cells. This vitamin exhibits only low immunogenicity and therefore high biocompatibility. Internalization of the nanoparticles is facilitated by binding to the membrane-bound folic acid receptor.

Surface modifications are also possible with lipophilic vitamins such as retinol, cholecalciferol, tocopherol and phylloquinone. Thus, for example, vitamin E can increase the cellular uptake of nanoparticles.

Fatty acids such as, for example, 1-octadecene or 18-methyleicosanoic acid and their derivatives, may increase solubility and stability of the colloids and have a terminal functional carboxyl group which may be utilized for subsequent binding of specific ligands. It is therefore useful to include fatty acids as modifiers.

Another embodiment of surface modification is a coating with polyalcohols such as, for example, diethylene glycol (DEG), which are particularly good at reducing unspecific protein adsorption. The same applies to polytetrafluoroethylene (PTFE, Teflon), in particular in its low molecular weight forms, which can achieve reduced protein adsorption. Polytetrafluoroethylene is frequently used in cardiosurgical applications.

Surface modifications can likewise be carried out using one or more naturally occurring amino acids which include both proteinogenic and non-proteinogenic amino acids, and synthetic amino acids. Both stereoisomers (D- and L-forms) may be used here. Di-, tri-, tetra- up to small polypeptides of the abovementioned amino acids hardly stimulate the immune system and are therefore likewise suitable for a thin compatibility layer. They may be artificial amino acid sequences as well as sequences from biological proteins. Peptide derivatives of natural proteins such as, for example, phytochelatin, may likewise be used for surface modification. Surface modification with Tat peptide and Tat peptide-containing peptides is another possibility of making nanoparticles available for the use in biomedical applications. The Tat peptide is an effective molecule, for example, for delivering gold nanoparticles through the cell membrane all the way into the nucleus.

Another embodiment of possible modifiers is the formation of a phosphorylcholine coating. Phosphorylcholine reduces a possible unspecific protein adsorption, for example on contact lenses. Owing to its non-thrombogenic properties, a phosphorylcholine modification can readily be employed in biological systems and is distinguished by a high storage stability.

Since polylactate is biocompatible, this substance is used in a variety of medical applications. More specifically, low molecular weight forms of polylactate constitute another possible surface modification of the nanoparticles of the invention. Both stereoisomers (D-/L-forms) may be employed here in order to reduce possible biodegradation.

Apart from the surface modifications mentioned, proteolytically cleavable binding of unspecific proteins to the nanoparticles is also possible. This may increase biocompatibility/compatibility. At the target location, the large protein may be removed with the small nanoparticles being released in the tissue. Said removal may also take place after an appropriate dwell time. Suitable for this are preferably commonly used proteins such as, for example, transferrin, lactoferrin, ceruloplasmin, elastin and albumin in addition to other proteins which reduce unspecific adsorption. Thus, for example, surface coating composed of combinations of polypeptides with elastin may prevent undesired clot formation and therefore increase the biocompatibility of the nanoparticles.

The major serum protein albumin may reduce non-specific interactions with plasma membranes. Furthermore, the appropriately modified nanoparticle retains the ability to develop specific interactions with target cells by a specific ligand simultaneously binding to the particle surface. A coating with serum albumin may result in a substantially longer blood circulation time by preventing a rapid uptake by microphages after intravenous administration, than is the case with uncoated nanoparticles.

Aside from the unspecific coatings outlined above, the nanoparticles of the invention carry a selective labeling with target cell-specific ligands; they are conjugated, for example, with proteins, antibodies, peptides or, particularly preferably, with small, high affinity protein domains, antibody fragments or other organic molecules which bind, for example, to tumor cell-specific structures or other targets. A preferred ligand is adhesin (see exemplary embodiment 4). "Specific" in this context means that the ligand is expressed on the target either exclusively or else to an increased extent.

The combination of reduced hydrodynamic diameter which results in the higher rates of diffusion and perfusion mentioned, together with the properties and improvements described above and the high fluorescence intensity, especially in the visible red light range, renders the nanoparticles of the invention a simple diagnostic agent which can be employed in many different ways for selective and accurate discrimination of tissue forms in vivo. These possibilities, in combination with antigen-specific biomarkers, are used especially for identifying CEA- and/or NCA-expressing cells, in particular for distinguishing abnormal, (pre-) carcinogenic tissue from normal tissue, assisting in the visual assessment during surgical intervention for a more precise tumor resection. The inventive nanoparticles employable herein therefore serve as contrast agents. This applies in particular to the use in bowel cancer diagnosis and surgery.

The nanoparticles having the modified adhesins according to the invention may be employed either as in vitro or as in vivo diagnostic agent, theranostic agent and/or therapeutic agent. For this purpose, they may be administered locally (e.g. intratumorally, intramuscularly or into surgically accessible tissues/organs) or else also systemically (e.g. intravenously). Local/topical administration may be provided for by way of a liquid, spraying solution, gel, foam, cream, active patch. This may be preferred in particular for the treatment/diagnosis of hollow organs such as in the case of bowel cancer. Oral intake is also possible, for example as syrup or in the form of tablets or capsules. Inhalation is equally possible (e.g. spray). Anal administration by suppository is envisaged. In one variant, the nanoparticles may be implanted in depot form.

The term "diagnostic agent" is used in the context of the present invention as a synonym for "contrast agent", i.e. it serves for the discriminating visualization of morphological or functional structures in biological systems, especially in living people, to assist a medical intervention.

The nanoparticles may be employed as diagnostic agent especially in surgical interventions. They can likewise be used in minimally invasive methods (e.g. endoscopy, laparoscopy). Combination with imaging methods such as PET, MRT, CT, etc. is worthwhile.

As already stated above, the use according to the invention in the form of local administration is particularly advantageous. The amount of Cd employed on local administration in this connection advantageously does not exceed one tenth of the total exposure which normally accumulate anyway during the course of life in the liver and kidney of a person of advanced age and usual lifestyle. The total exposure of these organs is about 18 mg (Saturag et al 2000; British Journal of Nutrition; 2000, (84), 791-802). Accordingly, it is advantageous on local administration for the amount of nanoparticles to be limited so that the amount of Cd supplied at least does not substantially exceed 2 mg. In a particularly preferred embodiment, tumor visualization is possible even with an amount of contrast agent which does not exceed a total amount of 0.6 mg, particularly preferably 0.2 mg, of cadmium.

"Local administration" means for the purpose of the invention any administration, on which an increased amount or dose of the contrast agent can be expected in distinct regions of the body depending on the manner of administration.

Accordingly a vascular administration of the contrast agent is also a local administration, if accompanying measures by the administering personnel, such as, for example, applying a ligature to afferent or efferent vessels, prevent the contrast agent from spreading across the blood vascular system in the body in an essentially unimpeded manner.

The particular advantage of this embodiment is that the use of the nanoparticles in medical application on a living person is thereby possible for the first time because otherwise—i.e. as systemic administration—this is precluded because of the toxicity associated therewith. This is because local administration reduces the dose of nanoparticles necessary for adequate visualization.

It has emerged that the Cd-containing contrast agent is advantageously employed according to the invention for visualizing a tumor in vivo in a dose corresponding to an amount of from 0.002 to 0.02 mg of Cd per $cm^3$ of tumor tissue. Dosages of the contrast agent of from 0.002 to 0.015 mg of Cd/$cm^3$ of tumor tissue are particularly advantageous, in particular those between 0.002 and 0.010 mg of Cd/$cm^3$. It is possible with this advantageous dosage to visualize tumors with a volume of up to about 150 $cm^3$ in vivo without thereby exceeding the normally acceptable upper limit of exposure for humans. The visualization of tumors with a volume of up to 50 $cm^3$ is particularly favorable.

The investigations may relate to all accessible tissues/organs of the patient, especially in the skin, hollow organs (e.g. in the gastrointestinal, urogenital, respiratory tract) or else externally accessible regions of the sensory organs and also the cardiovascular system.

Use as an in vitro diagnostic agent is also possible, for example immunohistochemistry or FACS, and ELISA. A combination of in vivo and in vitro diagnosis (e.g. biopsy material) is particularly advantageous.

The modified adhesins according to the invention may remain bound to the nanoparticles or may be removable or detectable or releasable.

BRIEF DESCRIPTION OF THE FIGURES

FIG. 1 SEQ ID NO 1;

FIG. 2 Multiple sequence alignment of adhesin groups;

FIG. 3 SEQ ID NO 2;

Figure 4:
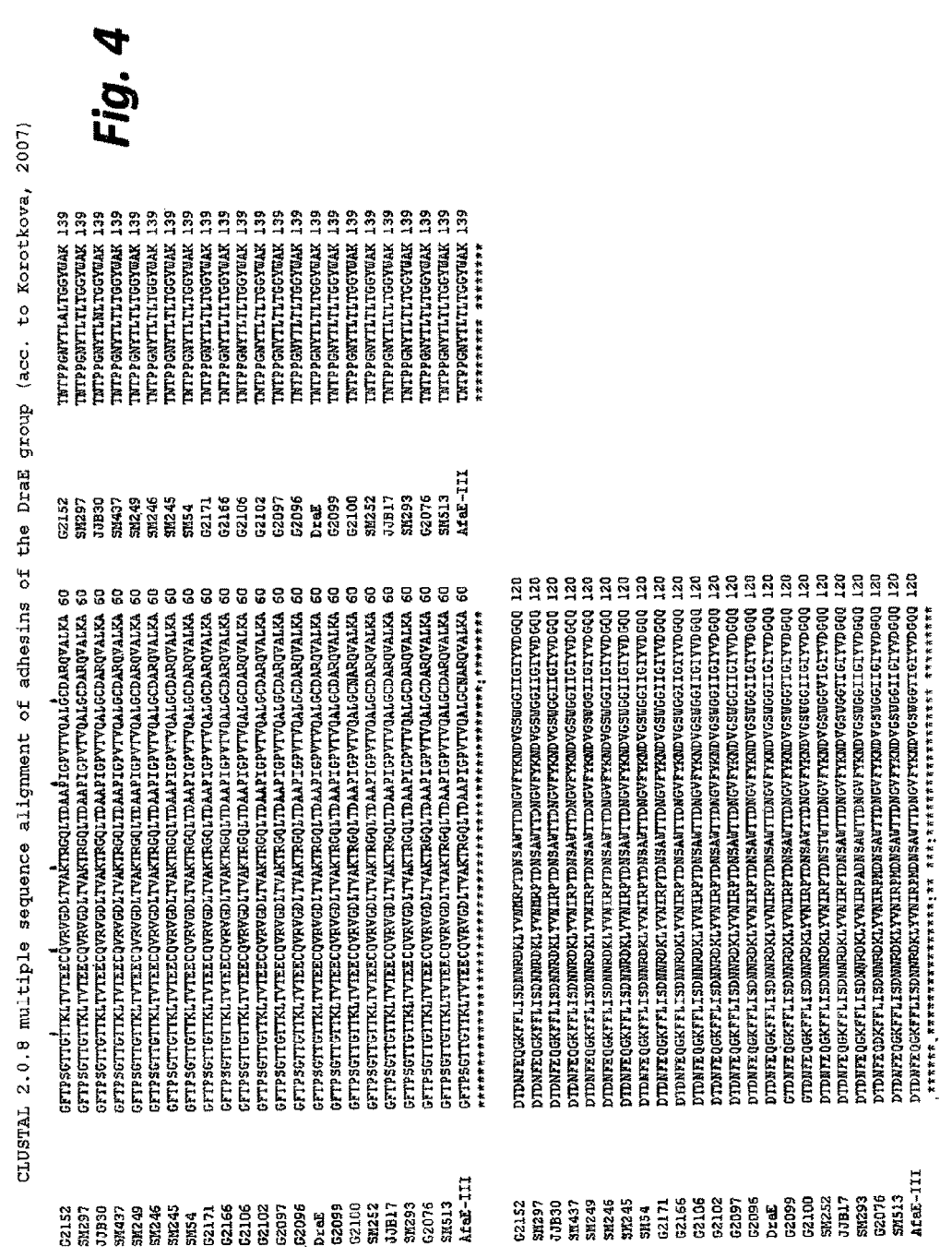

FIG. 4 Multiple sequence alignment of adhesion of the DraE group;

FIG. 5 SEQ ID NO 3;

FIG. 6 SEQ ID NO 4;

FIG. 7 SEQ ID NO 5;

Figure 8:
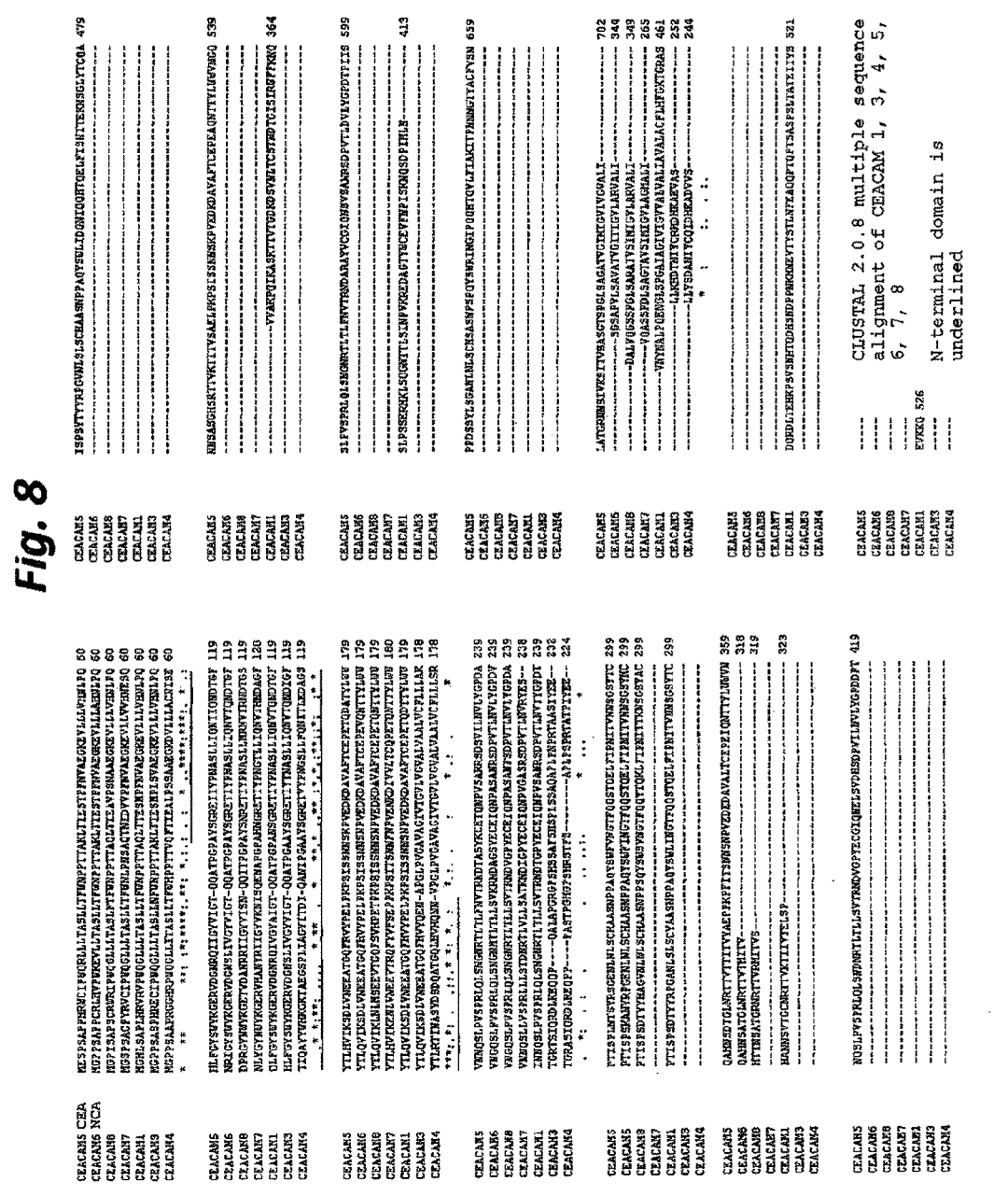

FIG. 8 Alignment of CEACAM proteins CEACAM 1, 3, 4, 5, 6, 7, and 8. The N-terminal domain as binding domain for the adhesins is underlined;

FIG. 9 N-terminal sequence of CEACAM proteins as derived from alignment of CEA AND NCA. The underlined sequence is only given in CEA;

FIG. 10 SEQ ID NO 7;

FIG. 11 SEQ ID NO 8;

FIG. 12 Adhesin having consensus sequence according to SEQ ID NO 9;

FIG. 13 SEQ ID NO 10;

FIG. 14 SEQ ID NO 11;

FIG. 15 SEQ ID NO 12;

DETAILED DESCRIPTION OF PREFERRED EMBODIMENTS

Exemplary Embodiments

I. Providing the Modified Adhesins

Figure 16:
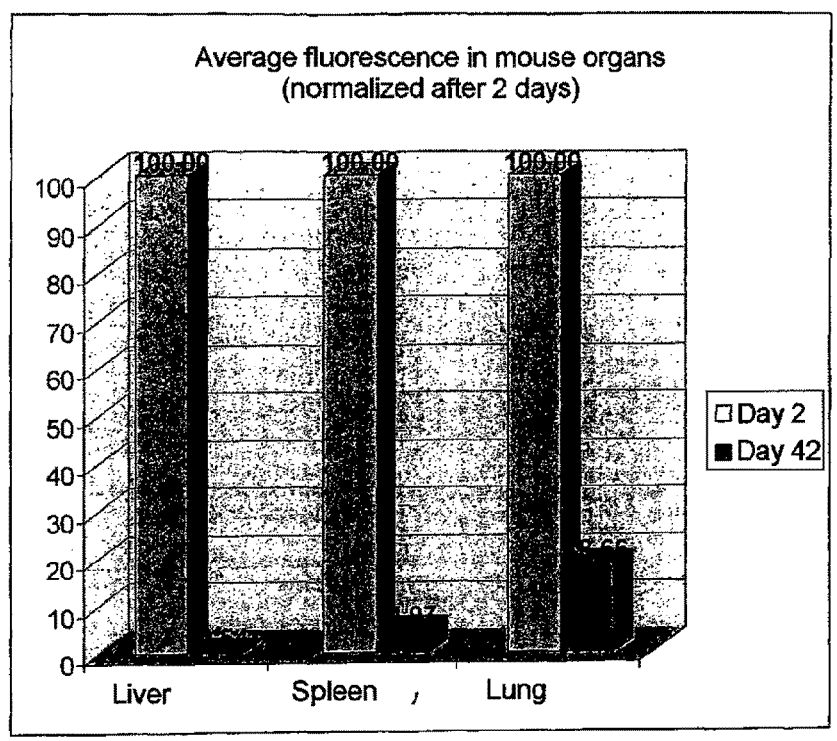
FIG. 16 Summary of detected fluorescence of liver, spleen, lung on day 42 as compared to day 2.

The N-terminal CEACAM, e.g. CEA, domain is sufficient for the binding of adhesives. This is known from binding studies using purified fimbriae which also contain the particular adhesin (Korotkova et al., The Journal of Biological Chemistry (2006) 281(39), pp. 29120-29139, "A Subfamily of Dr Adhesins of *Escherichia coli* Bind Independently to Decay-accelerating Factor and the N-domain of Carcinoembryonic Antigen"). The N-terminal domain of CEA and NCA (CEACAM6) was therefore employed as target for the adhesins according to the present embodiment.

To this end, the codon usage of the N-terminal domain of CEA and NCA and of the mature protein of DraE as ligand (adhesin) was optimized for expression in *Saccharomyces cerevisiae* beforehand. The genes were synthesized.

DraE constructs, preferably containing the mutation N77K, and the terminal domain of CEA (N-CEA hereinbelow) were cloned into yeast TH vectors and transformed into yeast.

The adhesin is subjected to mutagenesis, in a particularly preferred embodiment to an oligo-based, site-specific mutagenesis (e.g. EP1777292 A1). The library resulting therefrom is characterized by sequencing single colonies and the library DNA.

The library and the target (N-CEA) are transformed into the yeast strain Y190 which has been modified by integration of the Met1 gene (codes for a Uroporphyrinogen III methyl transferase) into the genome, and the yeasts are plated out on medium containing 25 mM 3-AT. The two proteins must interact for the reporter genes, Met1 and β-galactosidase, to be read.

Quantitative screening is carried out as described in EP1721974 A1. The Met1 reporter gene is detected by way of the fluorescence of the product, resulting from an enzymatic conversion of Uroporphyrinogen III.

To confirm the hits obtained, a further test was utilized prior to sequencing of the second reporter gene, lacZ. To this end, the activity of β-galactosidase was determined by means of converting the substrate FDG, by the enzyme into a fluorescent product, thereby reducing the number of hits to 25% prior to sequencing.

It is therefore possible to provide adhesin mutants which have improved affinity for CEA and/or NCA over the wild type, but in particular also over the template. The improvement in affinity—recorded, for example, as reporter gene readout according to the screening method disclosed in EP1721974 A1—over the template is at least about 5%, preferably at least 100%, particularly preferably even at least 300 or at least 500%. The affinity compared to the wild type may even approach here a value which is up to twice or else up to four times that of the template.

Particularly great improvements in affinity are achieved by combining at least two mutations, preferably also up to 3, 5 or 7 mutations. A particularly large increase in affinity is possible especially by repeating (optionally also several times) the screening step of EP1721974 A1.

The detection of improved mutants of different affinity is intended. It is important here to find the wild type in order to identify adhesins which are improved over said wild type. This covers the complete sequence space with affinity-improved mutants.

The modified adhesins of the invention which have been altered namely in one or more amino acid positions can be derived from these investigations.

1. Advantageous Modifications

Exemplary Embodiment 1

Position 88—Threonine

The mutation T88M is known from the literature (Korotkova et al., The Journal of Biological Chemistry (2006) 281 (39), pp. 29120-29139, "A Subfamily of Dr Adhesins of *Escherichia coli* Bind Independently to Decay-accelerating Factor and the N-domain of Carcinoembryonic Antigen") to cause in adhesins, especially in DraE, an increase in the affinity of said adhesin for CEA. Consequently, the position T88 was chosen for the first mutagenesis.

This and all subsequent information relate to the amino acid positions in DraE according to SEQ ID 1.

Quantitative screening was carried out as described in EP1721974 A1.

(i) Sequencing and Evaluation of Hits

Sequencing of the DNA from the hits after transformation into bacteria yields the following order of mutants with improved affinity for CEA, based on the frequency of identified hits: M>L>WT The most improved mutant in this position, T88M, was employed as template for the following mutageneses.

In addition, the mutation N77K was introduced in order to prevent the adhesin from binding to DAF (van Loy et al., Molecular Microbiology (2002) 45(2), pp. 439-452, "Identification of amino acids in Dr adhesin required for binding to decay-accelerating factor"). This mutation does not affect binding of the adhesin to N-CEA (Korotkova et al., The Journal of Biological Chemistry (2006) 281(39), pp. 29120-29139, "A Subfamily of Dr Adhesins of *Escherichia coli* Bind Independently to Decay-accelerating Factor and the N-domain of Carcinoembryonic Antigen" and own data). The template for the mutageneses below is therefore DraE T88M N77K.

Exemplary Embodiment 2

Position 7—Threonine

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: N>(F, C)>S>V>R, A>(I, L, Y)>WT Exemplary Embodiment 3

Position 17—Glutamate

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>P>K>G, D, R, N>Q>WT Exemplary Embodiment 4

Position 22—Arginine

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: T>A>S>N>K>WT Exemplary Embodiment 5

Position 25—Aspartate

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>G>N>A, T>K, R, H, Q, M>WT Exemplary Embodiment 6

Position 27—Threonine

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: K>R>L>V, Y>P, N, Q>WT Exemplary Embodiment 7

Position 28—Valine

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: W=F>WT Exemplary Embodiment 8

Position 29—Alanine

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: K>R>S>E, Q>F, G>L, H>P, N, T, W>WT Exemplary Embodiment 9

Position 31—Threonine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: G=D>S>N>WT Exemplary Embodiment 10

Position 34—Glutamine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: D>>G>S=N>L=V=T=A>WT Exemplary Embodiment 11

Position 37—Aspartate

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: N>>WT Exemplary Embodiment 12

Position 38—Alanine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: S=T>L>WT Exemplary Embodiment 13

Position 39—Alanine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: Q>S>D, M>G, F>WT Exemplary Embodiment 14

Position 41—Isoleucine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: V>>WT
In the rescreening by means of the FDG assay, the I41L clones had a higher readout than the I41V clones. Analyzing the sequence revealed that all of these clones also had the additional mutation V116A. I41L V116A therefore also represents an improved mutant.

Exemplary Embodiment 15

Position 47—Glutamine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: T>>N=C>S>G=A=P>WT Exemplary Embodiment 16

Position 52—Aspartate

Quantitative screening was carried out as described in EPI 721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: G>N, S>C, P, Q, Y, H, K, R, T>WT Exemplary Embodiment 17

Position 84—Asparagine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: D>>S>H>WT
The screening also found the (combination) mutant Q34L N84S which has a higher readout in the FDG rescreening compared to N84S.

This indicates that the combination of mutants results in a higher affinity for CEA in comparison with the single mutant.

Exemplary Embodiment 18

Position 86—Arginine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: V>>WT Exemplary Embodiment 19

Position 95—Threonine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: L>>M, Y, F>(C, W, Q)>N, E, S, I, H>WT
The combined mutant T95E T123I was also found; this combination had a higher FDG readout than the T95E mutant.
This indicates that the combination of mutants results in a higher affinity for CEA compared to the single mutant.

Exemplary Embodiment 20

Position 100—Phenylalanine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: Y>V>WT
The combined mutant F100S T11I D37G was also found; this combination had a higher FDG readout than the F100S mutant. Likewise, the combination mutant and F100I T123I was found which showed a higher FDG readout than the F100I mutant.
This indicates that the combination of mutants results in a higher affinity for CEA compared to the single mutant.

Exemplary Embodiment 21

Position 105—Valine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: S>A, T>R>M, V, P, N, E>Q, G, K, H>WT Exemplary Embodiment 22

Position 111—Isoleucine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: C>V>H>Y>T>M=F>WT Exemplary Embodiment 23

Position 114—Isoleucine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: V>>L>A=C>WT Exemplary Embodiment 24

Position 115—Tyrosine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: T=W>E>V>WT Exemplary Embodiment 25

Position 116—Valine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: A>S>L>WT Exemplary Embodiment 26

Position 118—Glycine

Quantitative screening was carried out as described in EP1721974 A1; in addition, a rescreening was carried out (see above).
(i) Sequencing and Evaluation of Hits
Sequencing of the DNA from the hits after transformation into bacteria yields the following order of mutants with improved affinity for CEA, based on the frequency of identified hits: P>S>WT
The combined mutant G118S I85L was also found; this combination had a higher FDG readout compared to G118S and was found among the first hits.

This indicates that the combination of mutants has a higher affinity for CEA compared to the single mutant.

Summary of Exemplary Embodiments 1 to 26

All of the following consensus sequences are specified based on the following sequence of DraE N77K (see also FIG. 1, SEQ ID No. 1):

GFTPSGTTGTTKLTVTEECQVRVGDLTVAKTRGQLTDAAPIGPVTVQALG

CDARQVALKADTDNFEQGKFFLISDNKRDKLYVNIRPTDNSAWTTDNGVF

YKNDVGSWGGIIGIYVDGQQTNTPPGNYTLTLTGGYWAK

These exemplary embodiments result in the following "positive" consensus sequence for those amino acids whose mutation within the adhesin gene results in an improved affinity of said adhesin for CEA:
Consensus Sequence SEQ. ID No. 9
$X_6$ T7(N, F, C, S, V, R, A, I, L, Y) $X_9$ E17 (S, P, K, G, D, R, N, H, Q) $X_4$ R22(T, A, S, N, K) $X_2$ D25(S, G, N, A, T, K, R, H, Q, M) X T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) X A39(Q, S, D, M, G, F) X I41(V) $X_5$ Q47(T, N, C, S, G, A, P) $X_4$ D52(G, N, S, C, P, Q, Y, H, K, R, T) $X_{31}$ N84(D, S, H) X R86V X T88(M, L) $X_6$ T95(L, M, Y, F, C, W, Q, N, E, S, I, H) $X_4$ F100(Y, V) $X_4$ V105(S, A, T, R, M, V, P, N, E, Q, G, K, H) $X_5$ I111(C, V, H, Y, T, M, $X_2$I114(V, L, A, C) Y115(T, W, E, V) V116(A, S, L) X G118(P, S) $X_{21}$ The alignment is depicted in FIG. 12.

In an advantageous embodiment, the modified adhesins according to the invention have one or more of the following amino acids: L26, G42, P43, V44, L49, D89, S91, S107, W108, G110. In a particularly preferred embodiment, all of these amino acids are present.

This results advantageously in a consensus as follows:
Consensus Sequence SEQ ID No. 10
$X_6$ T7(N, F, C, S, V, R, A, I, L, Y) $X_9$ E17 (S, P, K, G, D, R, N, H, Q) $X_4$ R22(T, A, S, N, K) $X_2$ D25(S, G, N, A, T, K, R, H, Q, M) L26 T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) X A39(Q, S, D, M, G, F) X I41(V) G42 P43 V44 $X_2$ Q47(T, N, C, S, G, A, P) X L49 $X_2$ D52(G, N, S, C, P, Q, Y, H, K, R, T) $X_{31}$ N84(D, S, H) X R86V X T88(M, L) D89 X S91 $X_3$ T95(L, M, Y, F, C, W, Q, N, E, S, I, H) $X_4$ F100(Y, V) $X_4$ V105(S, A, T, R, M, V, P, N, E, Q, G, K, H) X S107 W108 X G110 I111(C, V, H, Y, T, M, F) $X_2$ I114(V, L, A, C) Y115(T, W, E, V) V116(A, S, L) X G118(P, S) $X_{21}$ The alignment is depicted in FIG. 13. The advantageously present amino acids are underlined here.

It is advantageous, if the adhesins of the invention additionally have one or more, in particular all of the following amino acids: C19, C51, G106, Y128, T129.

Accordingly, the adhesins of the invention advantageously have a consensus as follows: consensus sequence 11 (see FIG. 14, all the advantageously present amino acids are underlined; combination of consensus structures 9 and 10 and the further amino acids preferred according to the above information):
Consensus Sequence SEQ ID No. 11 (FIG. 14):
$X_6$ T7(N, F, C, S, V, R, A, I, L, Y) $X_9$ E17 (S, P, K, G, D, R, N, H, Q) X C19 $X_2$ R22(T, A, S, N, K) $X_2$ D25(S, G, N, A, T, K, R, H, Q, M) L26 T27(K, R, L, V, Y, P, N, Q) V28(W, F) A29(K, R, S, E, Q, F, G, L, H, P, N, T, W) X T31(G, D, S, N) $X_2$ Q34(D, G, S, N, L, V, T, A) $X_2$ D37N A38(S, T, L) A39(Q, S, D, M, G, F) X I41(V) G42 P43 V44 $X_2$ Q47(T, N, C, S, G, A, P) X L49 X C51 D52(G, N, S, C, P, Q, Y, H, K, R, T) $X_{31}$ N84(D, S, H) X R86V X T88(M, L) D89 X S91 $X_3$ T95(L, M, Y, F, C, W, Q, N, E, S, I, H) $X_4$ F100(Y, V) $X_4$ V105(S, A, T, R, M, V, P, N, E, Q, G, K, H) G106 S107 W108 X G110 I111(C, V, H, Y, T, M, F) $X_2$ I114(V, L, A, C) Y115(T, W, E, V) V116(A, S, L) X G118(P, S) $X_9$ Y128 T129 $X_{10}$ 2. Particularly Preferred Combinations of Mutations The following combination of single mutants has proved to be particularly advantageous:

Mutagenesis of the wild-type adhesin DraE resulted in the improved mutant T88M (see exemplary embodiment 1), and further improved mutants were detected upon further rounds of mutagenesis using this mutant, DraE T88M (N77K), as template (see exemplary embodiments 2 to 26). Thus, for example, the multiple mutant DraE T88M (N77K) I111H was generated which exhibits a distinctly higher affinity for CEA compared to wild-type adhesin DraE and the DraE T88M mutant.

Another example is the construct DraE T88M Q34L N84S, which has a higher affinity for CEA than DraE T88M N84S (see exemplary embodiment 17). The combination mutant DraE T88M G118S I85L also has a higher affinity for CEA compared to the mutant DraE T88M G118S (exemplary embodiment 26).

The combination mutant F100S T11I D37G had an increased affinity for CEA in comparison with F110S (see exemplary embodiment 20). This was also the case for the combination mutant F100I T123I which had an increased affinity for CEA in comparison with F100I (see exemplary embodiment 20). The combined mutant T95E T123I was also found; this combination had a higher affinity for CEA than the T95E mutant (see exemplary embodiment 19).

Consequently, the object of the invention is solved by defining preferred embodiments of an improved adhesin ligand in respect of affinity for CEA and/or NCA, which embodiments in each case have any possible combination of the single mutants listed in consensus sequence 1.

The exemplary embodiments listed demonstrate that the nHybrid/Two-Hybrid screening method used herein enables combination mutants having increased affinities for CEA and/or NCA to be generated by carrying out repetitive cycles.

3. Multiple Mutagenesis

These experiments were carried out in the nHybrid system (EP1721974 A1).

Firstly, DraE T88M N77K I111V (TM=triple mutant) was employed as mutagenesis template, secondly DraE T88M N77K I111V I114V V116A (FM="Fünffachmutante" [quintuple mutant]) was used which has even higher affinity for CEA.

Exemplary Embodiment 27

Position 39—Alanine a) TM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>G>D=H>Q>WT With DraE T88M N77K as template, the order of improved mutants was Q>S>D>M>G>F, meaning that the TM probably has an altered structure which results in different mutants or the known mutants in a different order being found in position 39.

b) FM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>WT With DraE T88M N77K as template, the order of improved mutants was Q>S>D>M>G>F, meaning that the FM probably has an altered structure which results in different mutants or the known mutants in a different order being found in position 39.

c) Comparison of the Two Templates
  TM: S>G>D=H>Q>WT
  FM: S>WT

Exemplary Embodiment 28

Position 41—Isoleucine a) TM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: V>L>T>WT This means that a mutation at this site still improves the affinity for CEA, even with the TM as template; in this case, the same spectrum of mutants appears as with DraE T88M N77K as template. This fact suggests that the structural modification in the TM does not greatly affect amino acid position 41.

b) FM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: L>WT With DraE T88M N77K as template, L had been detected as a slightly improved mutant; V was the best mutant. This means that the FM probably has an altered structure which results in different mutants or the known mutants in a different order being found in position 41.

c) Comparison of the Two Templates
  TM: V>L>T>WT
  FM: L>WT

Exemplary Embodiment 29

Position 47—Glutamine a) TM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>A>C>T>WT With DraE T88M N77K as template, the order of improved mutants was T>N=C>S>G=A=P>WT, meaning that the TM probably has an altered structure which results in different mutants or the known mutants in a different order being found in position 47.

b) FM as Template

Quantitative screening was carried out as described in EP1721974 A1; in addition, a rescreening was carried out (see above).

(i) Sequencing and Evaluation of Hits

Sequencing of the DNA from the hits after transformation into bacteria yields the following order of mutants with improved affinity for CEA, based on the frequency of identified hits: S>WT With DraE T88M N77K as template, the order of improved mutants was T>N=C>S>G=A=P>WT, meaning that the FM probably has an altered structure which results in different mutants or the known mutants in a different order being found in position 47.

c) Comparison of the Two Templates
  TM: S>A>C>T>WT
  FM: S>WT

These exemplary embodiments again demonstrated that the nHybrid screening method used herein enables combination mutants with increased affinities for CEA to be generated by carrying out repetitive cycles.

3. Analysis of In Vivo Degradation of the Nanoparticles Employable According to the Invention by Means of High Content Screening The aim of this study was to detect the biological degradation of the dipeptide-coated nanoparticle (core: CdSe, shell: ZnS, maximum emission: 655 nm, hydrodynamic diameter of about 12.5 nm without protein ligand) in selected mouse organs by comparing the fluorescence on days 2 and 42 after intravenous injection of fluorescent nanoparticle conjugates at a dose of 1.7 mg/kg body weight.

Method

Six NMRI mice were injected with 1.7 mg/kg of body weight of the fluorescent nanoparticle conjugate (QD655#D416-36-KNH—protein ligand clone 5582 ("Fünfach-Mutante" FM [quintuple mutant], see above) via the tail vein. The mice were sacrificed on days 2 and 42, respectively, post injection, the organs were removed and shock-frozen at −80° C.

Sample Preparation:

200 mg of the particular organ were weighed and homogenized with 1 ml of 500 mM Bicine buffer (pH=8.3) in cryo tubes and 1 g of homogenization beads (MatrixD from MP Biomedicals) for 1 min, using the Fastprep24 (MP Biomedicals) homogenizer. The homogenate was put on ice.

Sample Embedding Mix (all Volumes in μl)

| | |
|---|---|
| BSA solution 30% | 106.4 |
| Homogenate | 213.6 |
| Glutaraldehyde solution 25% | 17.0 |

The BSA solution was introduced into an Eppendorf vessel, followed by addition of the homogenate, and the sample was cooled on ice for 2 min. This was followed by adding the glutaraldehyde solution and rapid mixing. In each case 200 μl of the samples were pipetted into a well of a microtiter plate with coverslip bottom (Greiner). Glutaraldehyde fixing took a few minutes and resided in a solid gel.

Measuring the Raw Data

Microscopy was carried out using the Olympus Scan^R system with a 60×/1.2 W lens. Images of the samples were generated using the Scan^R Acquisition software: 16 stacks per sample (=per well) were recorded with in each case 40 frames/stack and the frames spaced at 0.5 μm. The images were taken in 2 channels in parallel: the exposure time in the nanoparticle channel (emission filter 655/16) was 200 ms, and in the autofluorescence channel (emission filter 525/30) was 1000 ms.

Information Regarding Image Area and Volume:

| | |
|---|---|
| Width | 109 μm |
| Length | 109 μm |
| Height | 20 μm |
| Volume/stack | 2.38E-10 l |
| Total volume | 3.80E-09 l |

Evaluation of the Raw Data

The nanoparticles were quantified by means of Scan^R Analysis software. Firstly, maximum projection of the stacks was generated along the z axis onto a plane, followed by smoothing by means of rolling ball, and finally the weighted autofluorescence channel was subtracted from the nanoparticle channel. The intensity threshold for segmentation was set to 43.

The nanoparticles found were divided by means of gating into 3 categories (small, middle and big), with the criterion being the area of the nanoparticles found, within a sensible corridor defined by the mean intensity (gray scale values in the range of 60-400). The gates were rectangular and were defined as follows:

small: 4-35 pixels
middle: 36-400 pixels
big: 401-100 000 pixels

Most objects were found in the small gate, the fewest in the big.

Owing to the appearance of large and medium-large aggregates, an accurate quantitative statement is not possible because the number of individual nanoparticles forming each aggregate cannot be determined exactly. However, a qualitative statement on the nanoparticle distribution and pharmacokinetics can be made via the fluorescence as dimensionless parameter which is approximately proportional to the number of nanoparticles in an aggregate.

Calculation of the Dimensionless Fluorescence:

The number of objects is multiplied with the mean total intensity (average total fluorescence intensity per object) of the particular class of nanoparticles:

Objects×mean intensity=fluorescence

The fluorescence of homogenates from livers, spleens and lungs on days 2 and 42 was calculated and the average thereof were determined. Fluorescence on day 2 was normalized in each case to 100%.

The results are summarized in FIG. 16. According to this, only 0.54% of fluorescence was detectable in the liver, only 4.97% of fluorescence was detectable in the spleen, and only 18.66% of fluorescence was detectable in the lung on day 42 in comparison with day 2. This indicates that the adhesin-coupled nanoparticles of the invention are degraded in vivo.

What is claimed is:

1. A method of preparing a contrast agent for medical use comprising the steps of:

providing an adhesin comprising an amino acid sequence selected from the group consisting of the following sequences, DraE SEQ ID NO: 1 wherein said adhesin has one or more of the following mutations and is deleted N-terminally by up to 18 amino acids and/or C-terminally by up to 10 amino acids:

T7 (N, F, C, S, V, R, A, I, L, Y); E17 (S, P, K, G, D, R, N, H, Q); R22 (T, A, S, N, K); D25 (S, G, N, A, T, K, R, H, Q, M); T27 (K, R, L, V, Y, P, N, O); V28 (W, F); A29 (K, R, S, E, Q, F, G, L, H, P, N, T, W); T31 (G, D, S, N); Q34 (D, G, S, N, L, V, T, A); D37N; A38 (S, T, L); A39 (Q, S, D, M, G, F); I41 (V); Q47 (T, N, C, S, G, A, P); D52 (G, N, S, C, P, Q, Y, H, K, R, T); N84 (D, S, H); R86V; T88 (M, L); T95 (L, M, Y, F, C, W, Q, N, E, S, I, H); F100 (Y, V); V105 (S, A, T, R, M, V, P, N, E, Q, G, K, H); I111 (C, V, H, Y, T, M, F) I114 (V, L, A, C); Y115 (T, W, E, V); V116 (A, S, L); G118 (P, S), combining the adhesin with a suitable carrier for use as a contrast agent in medical treatment.

2. The method of claim 1, wherein the adhesin is conjugated to a nanoparticle.

3. The method of claim 2, wherein the nanoparticle has an inorganic core and a passivation layer, with the smallest diameter of an inorganic core including the passivation layer being no more than 15 nm.

4. The method of claim 1, wherein the adhesin is binding to the N-terminal sequence of a binding protein having an amino acid sequence selected from the group of the following sequences, CEACAM group SEQ ID NO. 5

CEA/NCA SEQ ID NO. 6

CEA SEQ ID NO. 7 and/or NCA SEQ ID NO. 8.

5. The method of claim 1, wherein said adhesin is deleted N-terminally by up to 12, and/or C-terminally by up to 8 amino acids.

6. The method of claim 1, wherein said adhesin is deleted N-terminally by up to 10 or 8, and/or C-terminally by up to 5 amino acids.

7. The method of claim 1, wherein the adhesin has one or more of the following mutations:

V28W; V28F; A39Q; A39S; I41L; Q47S; Q47T; I85L; T95L; G118S and T123I.

8. The method of claim 1, wherein the adhesin is used as a contrast agent in identifying bowel cancer in a medical treatment.

9. The method of claim 8, wherein the contrast agent is directed to CRC cells.

* * * * *